United States Patent [19]

Wesch, Jr.

[11] 4,281,535

[45] Aug. 4, 1981

[54] CYLINDER GRIPPING APPARATUS

[76] Inventor: William E. Wesch, Jr., P.O. Box 94162, Houston, Tex. 77018

[21] Appl. No.: 47,471

[22] Filed: Jun. 11, 1979

[51] Int. Cl.³ .................... G01M 3/28; B23B 31/16
[52] U.S. Cl. .................... 73/49.8; 73/49.5; 138/90; 269/139; 277/205; 279/119
[58] Field of Search ............ 73/49.8, 49.5, 49.6, 73/49.1; 138/90; 279/110, 118, 119, 121, 123; 269/139; 277/205, 206 R, 206 A

[56] References Cited

U.S. PATENT DOCUMENTS

| | | | |
|---|---|---|---|
| 3,434,337 | 3/1969 | Goeke | 73/49.8 |
| 4,077,250 | 3/1978 | Wesch | 73/49.8 |

Primary Examiner—Gerald Goldberg
Assistant Examiner—Joseph W. Roskos
Attorney, Agent, or Firm—Arnold, White & Durkee

[57] ABSTRACT

A cylinder gripping apparatus having a jaw, a body and a floating interfacing assembly having a curved surface bearing against an opposing surface or groove, the interfacing assembly being operable to generate a proportional gripping force in response to an axial force upon the cylinder to be gripped. The jaw is not connected to the body. The interfacing assembly is operable to permit a transverse displacement of the jaw.

45 Claims, 32 Drawing Figures

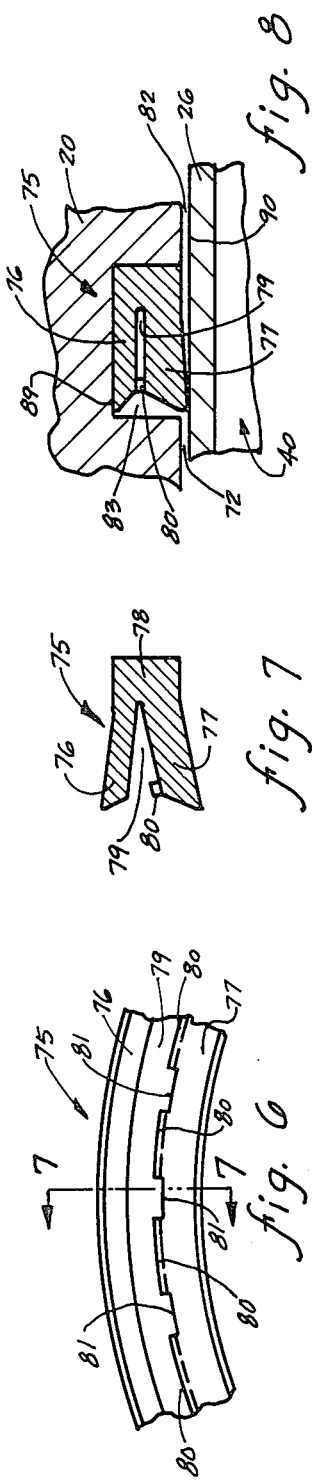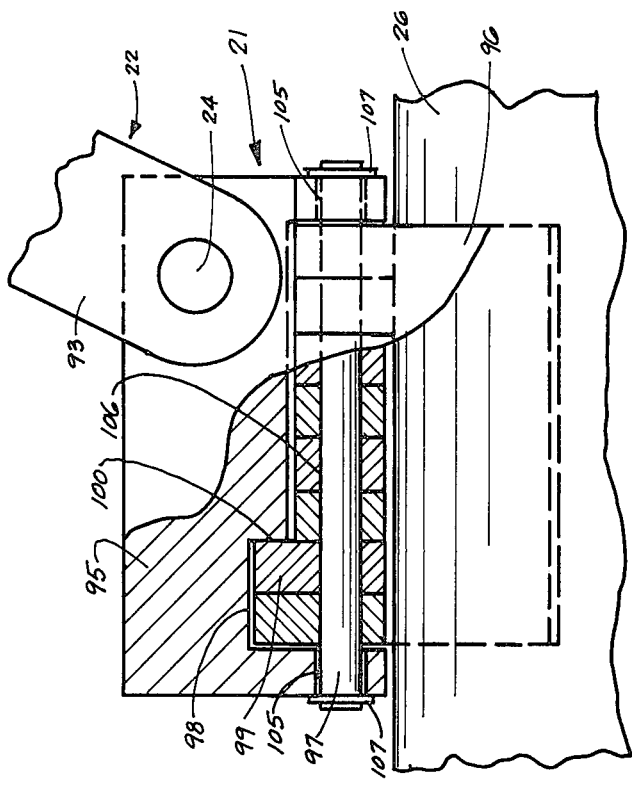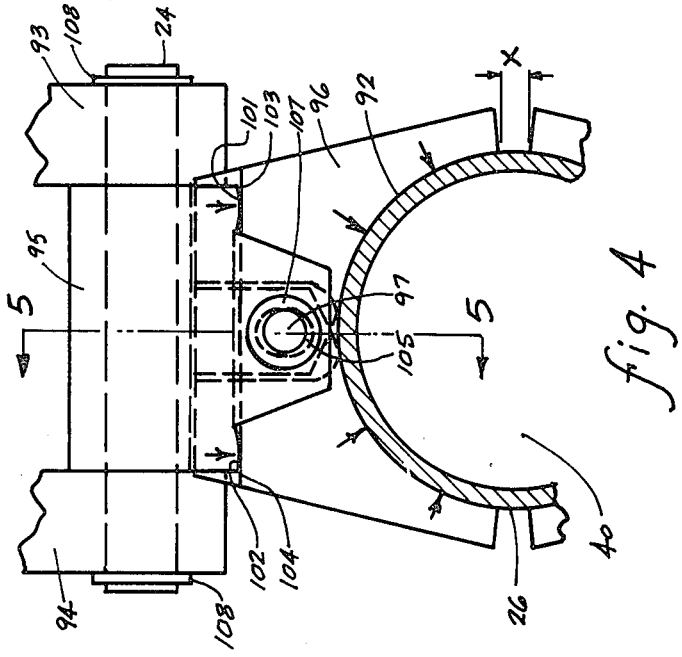

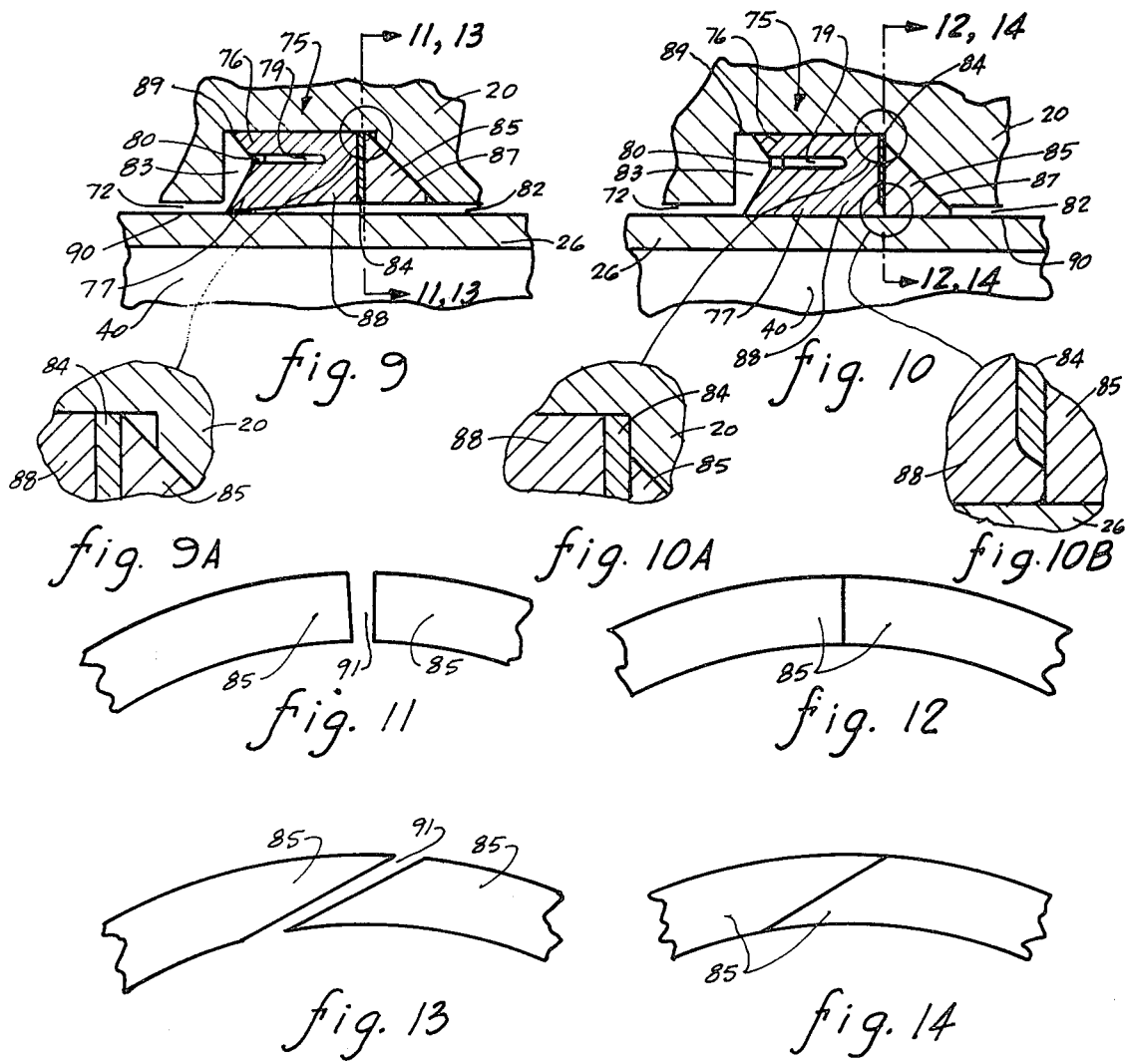
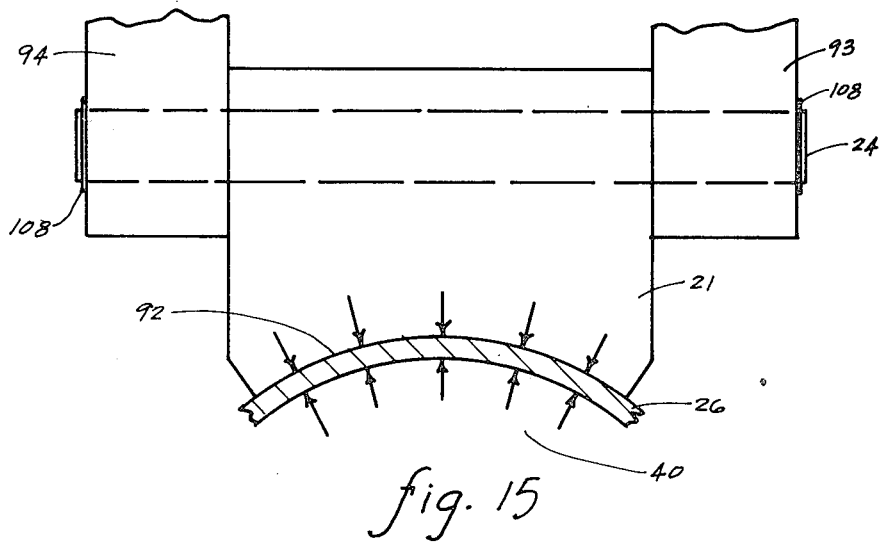

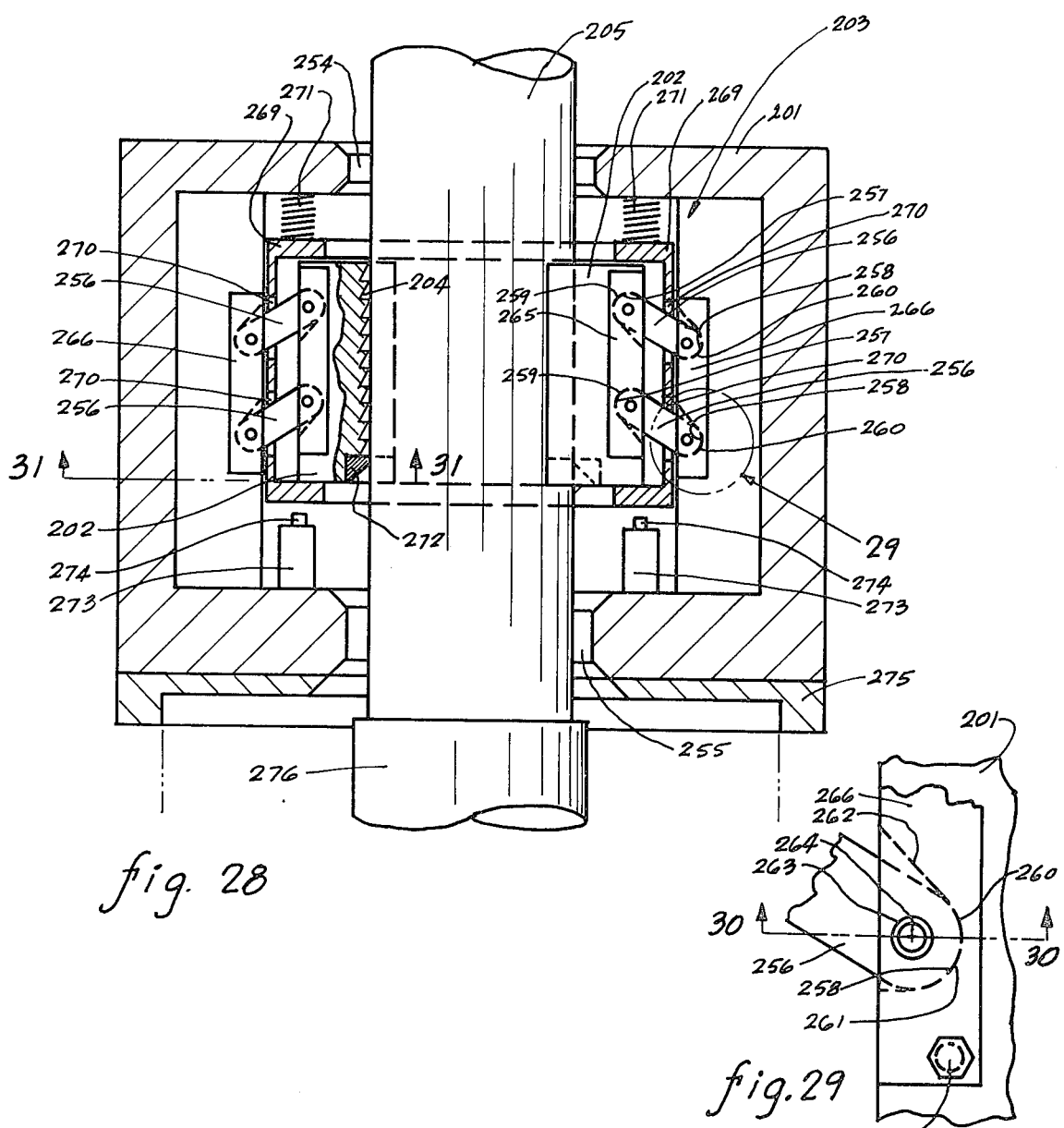
fig. 28
fig. 29
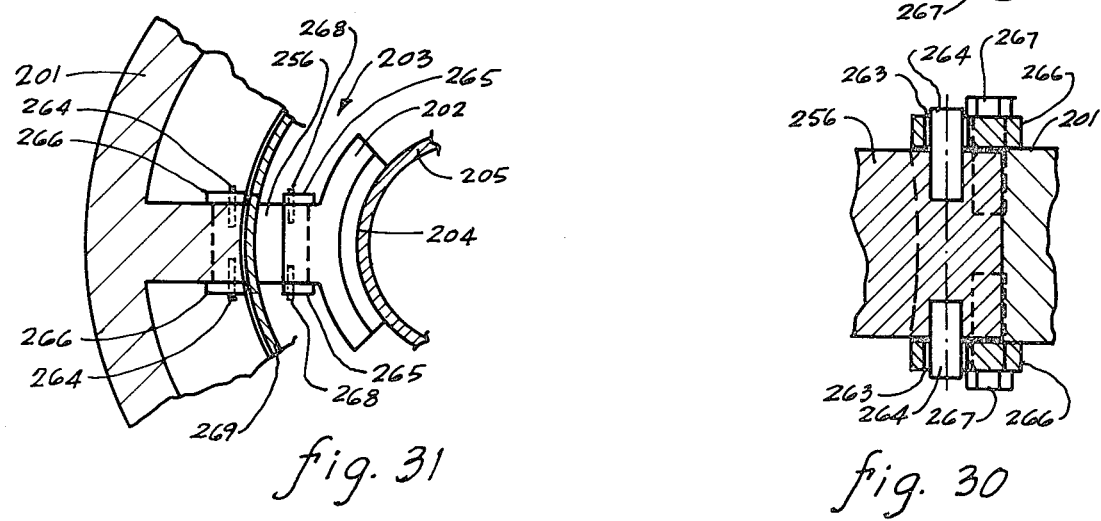
fig. 31
fig. 30

CYLINDER GRIPPING APPARATUS

CROSS REFERENCE TO RELATED APPLICATIONS

This application discloses subject matter related to U.S. Pat. application Ser. No. 037,140, entitled "Hydrostatic Testing Apparatus", filed May 8, 1979, having the same applicant, the disclosure of which is incorporated herein by reference. This application also discloses subject matter related to U.S. Pat. No. 4,077,250, issued to the same inventor on Mar. 7, 1978, entitled "Pipe Closure Apparatus", the specification of which is incorporated herein by reference.

BACKGROUND OF THE INVENTION

This invention relates generally to an apparatus for gripping a cylinder, pipe or tube. More particularly, this invention concerns an apparatus having a plurality of jaws adapted for gripping a cylinder, pipe or tube. The jaws are in operative association with a body such that the radial gripping counterforce exerted by the jaws upon the cylinder, pipe or tube is proportional to an axial force upon the cylinder tending to urge the cylinder in an axial direction with respect to the body. If the cylinder, pipe or tube attempts to move axially with respect to the body, an interfacing assembly urges the jaws into gripping engagement with the cylinder.

In a hydrostatic testing apparatus, it is necessary to grip a pipe or tube to be hydrostatically tested with sufficient force to sealingly engage the apparatus upon the pipe. It is necessary that the hydrostatic testing apparatus grip the pipe with sufficient force to reduce or minimize the danger of the pipe slipping out of the testing apparatus.

In the past, it has been common to grip a pipe or cylinder with hydraulic rams and threaded devices to slips which apply an outside force to hold a hydrostatic testing device or cap onto the pipe. Such devices must be tightened to the pipe under substantially zero internal pressure conditions because the slips must be firmly engaged before the pipe can be pressurized. Tightening during pressurization of the pipe is impractical and dangerous. During zero pressure conditions there is no internal fluid pressure to offset the clamping pressure or gripping force. Thus, such devices must necessarily stress the outer wall of the pipe while there is little or no internal pressure to offset the pipe gripping force. If the initial gripping force is inadequate, the hydrostatic testing cap will slip off during internal pressurization of the pipe. If the initial gripping force is excessive, the pipe may be deformed or weakened. For pressure testing, the jaws or slips of such devices must be initially tightened to a holding force sufficient to withstand test pressure before the pipe is pressurized.

U.S. Pat. No. 4,077,250, granted to applicant herein, discloses a pipe closure apparatus having gripper means connected to a spline or rib by means of a rotatable link attached to a mounting pin. This patent failed to disclose gripper means which are unconnected to a spline or rib, but which are interfaced with the spline or rib in a manner adapted to provide a radial counterforce which is proportional to the fluid pressure in the pipe.

The earlier patent teaches the use of a single rotatable link joining a gripper to a rib. A single link introduces stability problems and may create undesirable stresses upon the diameter of a pipe and the rib. Moreover, the earlier patent fails to address the unexpected uneven distribution of the load forces upon the pipe achieved by the gripper means disclosed in that patent where the gripper means is not permitted to move generally parallel to the axis of the pipe, or to move transversely with respect to the axis of the pipe.

In prior art jacking systems for offshore oil drilling platforms, it has been common to grip platform legs with shear pins, slips or hydraulic rams. Such hydraulic rams shear pins or slips had to be manually set. The gripping force upon the platform leg was not necessarily related to the weight of the platform deck. Oftentimes, a drilling platform becomes unleveled such that the forces upon other platform legs may increase substantially. Existing devices for leveling a platform require the gripping means to be released from a platform leg before leveling forces can be applied. Releasing the gripping means from one platform leg in order to permit leveling necessarily increases the danger of the platform sliding down the platform leg and creating stress upon the remaining platform legs. Releasing the gripper means for leveling purposes creates a danger of platform system failure.

In addition, if one jacking device failed, the stress upon the remaining platform legs could increase substantially. The failure of jacking systems presents a serious hazard to offshore drilling operations. When the stress upon prior art jacking devices increases, there is no mechanism to assure that the gripping force upon the platform leg will also increase in response to such stresses.

Prior art jacking systems are also unsatisfactory in that many such systems require that shear pin holes be aligned or that gears be meshed. Thus, the platform may not be jacked and leveled by moving the platform any desired distance. The platform may be moved only from one pin hole to another.

Prior art blowout preventer devices, used to prevent pipe from being blow out of a hole during drilling operations typically use hydraulic or threaded systems to grip the pipe. Such prior art systems must be set by external gripping forces. Such devices oftentimes cause hoop stresses upon the pipe when engaged. Because the gripping force is not related to the force tending to push the pipe out of the hole, the pipe must be gripped with an adequate force to prevent a blowout regardless of the existence of any downhole pressure. Thus, under substantially zero downhole pressure conditions, the pipe tends to be overstressed. Moreover, existing systems may be slow to engage. Prior art blowout preventer devices require manual setting and are not automatic or self-engaging.

If a large downhole pressure suddenly develops, there is no mechanism in such prior art blowout preventer devices to automatically set or increase the gripping force. Thus, such prior art devices are ineffective to prevent a blowout unless they have previously been set upon the pipe with sufficient force to withstand the sudden increase and in downhold pressure. Such prior art blowout preventers must also be released in order to permit the withdraw of casing, coupling or upset portions on the drill string.

Prior art hanging systems for pipe, tubing and casing, such as systems employed to prevent pipe from being dropped down into a hole during workover and drilling operations, commonly referred to as "hangers", and systems used to grip pipe going in and out of a well, commonly referred to as "elevators" or "snubbers", required that an expensive derrick be constructed at the drill site in order to permit operation of the hanging device. Such prior art devices typically employ slips that must be manually reset. In order to pass casing, coupling or upset portions of the pipe or drill string, such prior art devices require that the slips be released and expanded to permit the pipe and casing to be passed. While the slips are released for the passage of the casing, the safety hanging device is inoperative. Thus, during such periods, the pipe or drill string is exposed to the risk of being dropped into the hole.

The adverse economic consequences and delays encountered when drill pipe or other devices are dropped into a hole and the difficulty of retrieving the pipe or such devices requires that a safety hanging apparatus be available to guard against dropping the pipe at all times during drilling operations.

In addition, many prior art hanging devices, including snubbers, elevators and hangers, cannot take upward pressure upon the pipe without impairing their operation.

While prior art arrangements have exhibited a degree of utility in gripping a pipe, cylinder or tube, room for significant improvement remains. The problems enumerated in the foregoing are not intended to be exhaustive, but rather are among many which tend to impair the effectiveness of previously known devices for gripping cylinders or pipes. Other noteworthy problems may also exist; however, those presented above should be sufficient to demonstrate that the prior arrangements appearing in the art have not been altogether satisfactory.

This invention relates generally to an apparatus for capping and sealing the end of a pipe, tube or cylinder during hydrostatic testing. More particularly, this invention concerns an apparatus having a plurality of jaws pivotally mounted on a plurality of arms, and the arms are in turn pivotally mounted to a body adapted to axially receive a pipe, tube or cylinder. With jaws of an area determined in accordance with the present invention the mechanical pressure upon the outer wall of the pipe substantially equals or is proportional to the fluid pressure upon the inner wall of the pipe. Therefore, the wall of the pipe is compressed; the outer diameter of the pipe is not substantially stressed. The apparatus is adapted to cap the pipe during hydrostatic testing without generating significant hoop stresses upon the pipe itself.

While the present invention is described with referenced to capping a pipe, it is intended that "pipe" wherever used herein shall include tubing or other cylindrical objects. The invention may also facilitate grasping a cylindrical object for other purposes.

Hydrostatic testing of pipes, upset tubing, and other cylindrical objects is necessary to insure that the pipe or tubing will withstand pressure levels equal to or greater than those which are expected to be encountered during use. Hydrostatic testing is generally a requirement of the American Petroleum Institute (A.P.I.) for most types of pipes.

In the absence of adequate hydrostatic testing during the installation of a petroleum or oil by-product pipeline, hidden flaws in the pipe may cause it to burst. An erupted pipe may go undetected for relatively long periods of time and loose a significant portion of its contents, which may have adverse consequences for the environment. In addition, the adverse economic consequences involved in repairing a broken pipeline and the consequential down time can be severe. The resultant disruptions in the supply of oil, natural gas, or other commodity intended to be transported through the pipeline, in addition to the foregoing, require pipe and tubing to be adequately tested hydrostatically prior to or during the installation of such pipeline.

Manufacturing operations for producing pipe or tubing expected to withstand pressure during use require hydrostatic testing as a quality control measure. Unless pipe and upset tubing are tested, undetected flaws can create serious safety hazards to an end user. Therefore, hydrostatic pressure testing has become a practical necessity for pipe, fittings and tubing after fabrication.

In the past, it has been common to weld a cap onto the end of a pipeline or an unthreaded or unflanged pipe to be tested. Welding requires expensive skilled labor to perform the welding operations. This work cannot ordinarily be performed by unskilled laborers. The cap must be securely welded to withstand test pressurization without blowing off of the end of the pipe. In some cases, stress relieving and X-raying of the welded cap is required. After testing, the cap must be cut off of the pipe. Not only is welding time-consuming and expensive, but also, the danger of explosion in some environments may be so great that welding operations are not feasible.

Prior art devices have included caps adapted to be screwed onto the end of the pipe or tubing to be tested. Such devices utilize the threads of the pipe to secure the device to the pipe. It is believed that API specifications require that such devices be tightened hand-tight only. Otherwise, the threads of the pipe may be damaged. However, a hand-tight cap will not withstand high pressure testing. Thus, to achieve a satisfactory seal, such devices are often overtightened resulting in stripped threads and damage to the pipe or fitting. Threads unknowingly stripped during installation present a latent danger that can kill or injure if pressurization causes the cap to blow off of the end of the pipe during testing. Such devices may not have the structural integrity to withstand testing pressures and may be blown off, thus presenting a serious threat of injury.

Moreover, such devices must be tightened under substantially zero internal pressure conditions because tightening during pressurization is impractical and dangerous. During zero internal pressure conditions there is no internal fluid pressure to offset the clamping pressure. Thus, the threads and other portions of the pipe must be stressed, and damage to the pipe or threads may result. Clearly, such prior art devices are unusable on pipe with damaged threads or no threads at all. It is often impractical to machine new threads onto the end of the damaged pipe because of the costs and delay involved. Thus, the cost of pipe ruined by such devices renders these known devices impractical in many cases.

In order to safely perform a hydrostatic test, all air and other gaseous matter must be expunged from the inner volume of the pipe. Failure to remove substantially all of the air creates an explosion hazard that can pose a serious danger to anyone in the vicinity of the testing apparatus. Most prior art devices fail to have a positive safeguard against such trapped air type explosions.

For example, in the past it has also been common to attach a cap onto the end of a pipe with bolts, screws, or other fastening means. Such methods of capping a pipe have been unsatisfactory, however. Not only are such methods time-consuming, but injuries and even deaths can result from such caps being blown off of the pipe during high pressure testing, because such methods and apparatus fail to provide a satisfactory means for eliminating air or gas from the interior of the pipe.

Known methods of removing air from a pipe include tilting the uncapped end of a joint of pipe in an upward direction, thereby causing air bubbles to migrate to the raised end of the pipe. Such tilting methods often result in pipe handling problems because the pipe may slip or be dropped. The expense and time required for such handling methods, in addition to the hazard posed when such pipe is dropped or slips, renders such methods unsatisfactory. Moreover, long sections of pipeline cannot be conveniently tilted or may be too long for the pipe handling apparatus available.

Another example of a prior art mechanism utilizes a set of independently operated jaws. Each jaw is manually tightened against the pipe by means of a screw or bolt which is adjusted with a wrench to jam the jaw against the pipe wholly independently of the other jaws. This type of mechanism is unsatisfactory at least insofar as it may create hoop stresses or deformations upon the pipe. For high pressure testing, the jaws must be tightened to a holding force sufficient to withstand test pressure before the pipe is pressurized. This imposes excessive stresses on the walls of the pipe which are likely to overstress, deform or weaken the pipe.

Other devices employ hydraulic rams and threaded devices to slips which apply an outside force to hold the cap onto the pipe. Necessarily, such devices must stress the outer wall of the pipe while there is little or no internal pressure to offset the pipe gripping force. If the initial gripping force is inadequate, the cap will slip off during internal pressurization of the pipe. Such known devices have a tendency to deform or damage the pipe.

Representative prior art patents illustrating problems of the type overcome by the present invention are U.S. Pat. Nos. 2,699,802; 3,647,108; 3,765,560; 3,885,521; 1,746,071; 2,399,544; 2,445,645; 2,480,358; 2,851,061; 3,108,012; 3,125,464; 3,525,111; and 3,703,947.

U.S. Pat. No. 4,077,250, granted to applicant herein, discloses a pipe closure apparatus having gripper means connected to a spline or rib by means of a rotatable link attached to a mounting pin. This patent failed to address the problem of removing air from the pipe in order to reduce the hazard of explosion. Moreover, this patent fails to address the problem of extrusion of the seal during high pressure testing.

The earlier patent disclosed an alignment ring positioned axially to the rear of a gripper means. The rotatable link was attached to a spline or rib, which was in turn joined to the body or closure plate. However, this arrangement was found to be unsatisfactory in some instances. When pressure is introduced into the pipe, the gripper means is urged in a direction generally toward the rear of the body. The gripper means therefore urges the spline or rib generally radially outward. Difficulties were encountered in manufacturing a commercially practical spline or rib adequate to withstand the radially outward force generated by the gripper means during high pressure testing. It was found that an enormous rib was required to withstand high pressure testing because of the manner in which the load was transmitted to the rib in the earlier patent.

The prior art patent also has failed to address the problem created by dirt, grime or air which may become entrapped within a U-shaped seal. The entrapment of air, dirt, debris or other foreign matter within a seal may inhibit, if not render inoperative, the intended operation of the seal. Nor did the earlier patent have a pre-loaded lip to assure zero leakage during low pressure filling of the pipe.

The earlier patent was not adapted for testing pipe with upsets, bell ends or coupling ends. In order to pass such pipe ends, the alignment ring had to be made too large to effectively align the pipe during testing. That patent had no centralizer means for centering such a pipe after passing the larger end of the pipe.

The earlier patent teaches the use of a single rotatable link joining a gripper to a rib. A single link has proved to be unsatisfactory in some instances. A single link introduces stability problems and may create undesirable stresses upon the diameter of a pipe and the rib. Moreover, the earlier patent fails to address the unexpected uneven distribution of the load forces upon the pipe achieved by the gripper means disclosed in that patent where the gripper means is not permitted to move generally parallel to the axis of the pipe.

The prior patent was not adaptable to test several different pipe sizes with a single apparatus. The prior patent failed to provide means for readily adapting the apparatus to fit different pipe sizes.

While prior art arrangements have exhibited a degree of utility in capping the end of a pipe or tube to permit hydrostatic testing, room for significant improvement remains. The problems enumerated in the foregoing are not intended to be exhaustive, but rather are among many which tend to impair the effectiveness of previously known apparatus for capping pipes. Other noteworthy problems may also exist; however, those presented above should be sufficient to demonstrate that the poor arrangements appearing in the art have not been altogether satisfactory.

SUMMARY OF A PREFERRED EMBODIMENT OF THE INVENTION

Recognizing the need for an improved apparatus for gripping a cylinder or pipe for hydrostatic testing for jacking operations upon offshore drilling platforms, for gripping drill pipe to prevent a blowout and for gripping drill pipe, tubing and casing in safety hanging systems and other wellhead workover applications, it is, therefore, a general intent in disclosing the present invention to provide a novel apparatus for gripping a cylinder, pipe or tube, which minimizes or reduces the problems of the type previously noted. The present invention has further useful application in gripping a pipe, tube or cylinder for other purposes.

A feature of the cylinder gripping apparatus resides in the ability to permit the cylinder, pipe or tube to move in one direction with respect to a body, and to prevent the cylinder from moving in a second opposite direction with respect to the body. A correlated feature resides in the ability of the cylinder gripping apparatus to grip the pipe with a force which is proportional to the axial force upon the pipe tending to move the pipe with respect to the body. In an application as a blowout preventer, the cylinder gripping apparatus includes the more detailed feature of increasing its grip upon the pipe in response to an increase in downhole pressure tending to forced the pipe out of the well. Thus, a sudden increase in downhole pressure will result in a sudden increase in the gripping force upon the pipe.

A feature resides in the provision of floating lugs which allow jaws to grip a cylinder, pipe or tube with a proportional gripping force which opposes rotational movement of the cylinder.

In an application as a snubber, the invention includes the feature of back-to-back gripping apparatus which grip pipe in both axial directions while tubing is installed or removed. One set of back-to-back gripping apparatus holds the tubing while another back-to-back apparatus reciprocates axially to jack the tubing in or out of the well. During this operation, the tubing is secured at all times in both axial directions. The gripping means of the present invention has the additional feature of incorporating lugs which will not only grip the pipe axially but will grip the pipe with a force proportional to a rotational torque for making up or unscrewing joints of pipe.

Of independent significance, the gripping apparatus includes an interfacing assembly which is more economical to construct and operate. A more detailed feature resides in the utilization of force translation lugs to interface the jaw with the cylinder. The utilization of such force translation lugs renders the cylinder gripping apparatus inexpensive to construct and simple to operate.

Yet another feature of the cylinder gripping apparatus is the provision for an interfacing assembly which permits the jaw to be easily aligned with the cylinder, even when the cylinder is not axially centered within the body. The interfacing assembly permits radial, axial and transverse movement of the jaw with respect to the body in order to permit the jaw to correctly align itself upon the cylinder.

In an application as a drilling platform jacking apparatus, the cylinder gripping apparatus includes the related feature of providing a jacking apparatus which increases its grip upon the platform leg in response to increased pressures generated by unleveling of the platform deck or the failure of a jacking apparatus upon another leg of the platform. This feature reduces the incidence of failure of the jacking apparatus.

A cylinder gripping apparatus according to a presently preferred embodiment of the invention intended to substantially incorporate the foregoing features includes a jaw adapted for gripping a cylinder, a body adapted to axially receive the cylinder, and an interfacing assembly. The interfacing assembly is interposed between the jaw and the body and is adapted to urge the jaw into gripping engagement with the cylinder when the cylinder is urged in a first direction with respect to the body. The interfacing assembly is adapted to allow the jaw to release from the cylinder when the cylinder is moved in a second direction with respect to the body.

The interfacing assembly is adapted to provide a radial gripping force in response to an axial force upon the cylinder which is proportional to that axial force. The interfacing assembly is adapted to permit radial, axial and transverse movement of the jaw with respect to the body in order to permit the jaw to align itself upon the cylinder when the cylinder is not perfectly centered within the axis of the body or when the cylinder is deformed.

The interfacing assembly may comprise a force translation lug which is engagable within bearing grooves upon the jaw and the body.

The interfacing assembly may also comprise a plurality of generally cylindrical rollers interposed between the jaw and the body. In this embodiment, the body has an inclined side wall. The rollers are operable to facilitate the movement of the jaw relative to the body along the inclined side wall of the body in order to urge the jaw into gripping engagement with the cylinder. Channels adapted to receive the cylindrical rollers may be formed either in the jaw or in the side wall of the body.

The interfacing assembly may alternatively comprise a cam arm pivotally attached to the body having a generally arcuate cam surface. The jaw may have a groove adapted to receive the cam surface of the cam arm. The cam arm is operable to urge the jaw into engagement with a cylinder when the cam arm is rotated with respect to the body.

Employed as a platform jacking apparatus, the cylinder gripping apparatus may employ two sets of jaws. One set of the jaws is operable to grip the platform leg while the other set is released. Actuating means or hydraulic cylinders are connected to one set of the jaws to provide a means for jacking the platform deck up upon the platform leg.

Examples of the more important features of this invention have thus been summarized rather broadly in order that the detailed description thereof that follows may be better understood, and in order that the contribution to the art may be better appreciated. There are, of course, additional features of the invention that will be described hereinafter and which will also form the subject of the claims appended hereto. Other features of the present invention will become apparent with reference to the following detailed description of a presently preferred embodiment thereof in connection with the accompanying drawings, wherein like reference numerals have been applied to like elements.

Recognizing the need for an improved method and apparatus for capping an end of a pipe for hydrostatic testing, it is, therefore, my general intent in disclosing the present invention to provide a novel method and apparatus for capping an open end of a pipe, which minimizes or reduces the problems of the type previously noted. The present invention has further useful application in gripping a pipe, tube or cylinder for other purposes.

A feature of the capping apparatus resides in a particular geometric arrangement of the arms, jaws and body, such that during hydrostatic testing, hoop stresses or undesirable forces imposed by the jaws and arms onto a pipe are minimized. A further feature of the invention resides in a novel centralizer adapted to axially center the pipe within the body of the apparatus.

Yet another feature of the invention resides in the novel arrangement of an air purge valve with passageways interconnecting the valve to a pressuized region within the interior region of the body in the pipe. The purge valve is adapted to expunge trapped air from the pressure zone. This feature reduces the hazard of explosions caused by air feature reduces the hazard of explosions cause by air trapped within the pressurized region within the interior of a pipe capped in accordance with the invention.

An additional feature of my invention resides in the adaptability of the apparatus to a wide range of pipe diameters and pipe surfaces. Replaceable jaw tooth segments, interchangeable cam piece surfaces, and adapters facilitate the hydrostatic testing of varying pipe sizes and permit the movement of pipe couplings, upsets and bell ends through or into the apparatus of the present invention.

Of independent significance is the feature residing in the novel arrangement of a flexible member seal, a spacer and a ring. The ring is adapted to slide into contact with the pipe surface and prevent the extrusion of the seal during high pressure testing.

Another feature pertains to the particular arrangement for connecting the jaw tooth segment to an arm.

A further feature of my invention resides in the ability to hydrostatically test pipe or tubing without deforming the pipe or tubing, even under high pressure testing. The mechanical force per square inch applied to the surface of the pipe by my testing apparatus is proportional to the invention pressure per square inch of the fluid or water upon the inside surface of the pipe. Thus, as a practical matter, only the wall of the pipe is compressed by proportionally opposite pressure forces; the outer diameter of the pipe is not substantially stressed.

Of independent significance is the feature pertaining to the novel means for engaging and disengaging the jaws upon the pipe. This feature resides in the quick placing of the apparatus upon the pipe to easily secure a safe sealing engagement of the end of the pipe and to minimize the time required to handle the apparatus. An engagement means is disclosed for accurately aligning the jaws with synchronized sleeves.

In using the apparatus of this invention, nothing is screwed on the pipe or tubing, nothing is screwed off, and nothing is forced onto the pipe or tubing. Threads are not necessary to facilitate capping in the pipe. Existing threads are not used. No significant outside force is required to hold the testing apparatus to the pipe or tubing. The force applied to hold the apparatus to the pipe is self generating and is always proportional to the internal pressure of the pipe, providing an added safety feature: the greater the pressure, the harder the holding force.

Moreover, a feature of my invention pertains to the ability to test over upsets, threads and couplings. A related feature is the ability to cap the end of the pipe without damaging the pipe threads or couplings.

A collateral feature of my invention is the speed and ease with which pipe or tubing may be tested. Skilled welders are not required. Untrained workers may easily, quickly and safely install my apparatus to pipe or tubing. Many man-hours may be saved. The apparatus may be operated for long periods with minimal wear and maintenance. Hydrostatic testing may be performed quickly, economically and safely.

A further feature of my invention resides in the adaptability of the apparatus to serve as an end closure. Appropriate means may be provided to join two of my apparatus together with a bore through the front wall of the caps to provide a weldless joint between two pipe sections for connecting such pipe when welding operations are not feasible, due to the danger of explosion or otherwise. A valve or other device may also be attached to the end of a pipe.

Another feature of may invention resides in the operability of my apparatus despite the presence of oil, dirt, rust or mill scale on the pipe. The jaw tooth segment is adaptable to grip such pipe; and the seal is operable to seal such pipe.

Finally, a feature of my invention pertains to the adaptability of my apparatus for hydrostatically testing a varity of pipe end types, including, for example, plain end pipe, threaded pipe, threaded casing, threaded non-upset tubing, threaded pipe with made-up coupling, casing with made-up coupling, upset tubing with made-up coupling, non-upset tubing with made-up coupling, external upset tubing with and without made-up coupling, and bell end pipe. It will be appreciated that other types of pipe, tubing or other cylindrical objects may also be capped or held with the disclosed invention.

A pipe capping apparatus according to a presently preferred embodiment of the invention intended to substantially incorporate the foregoing features includes, in addition to the elements enumerated above, a body and a plurality of jaws mechanically coupled through a radial translator adapted to translate an axial pressure force upon the body into a radial force that is evenly applied to the outside wall of a pipe. The body, radial translator and jaws operate to sealingly hold the end of the pipe to facilitate pressurization. A pressure barrier apparatus comprising a flexible seal, and a spacer and an extrusion inhibiting ring included for high pressure testing, cooperates in sealingly engaging the pipe.

More specifically, the flexible seal has a pair of lips formed upon a seal body. The lips define a pressure zone between the lips that also facilitates flushing debris, dirt and rust from the seal and allows trapped air to escape. Lugs upon the seal pre-stress the seal to facilitate initial engagement of the lips.

A tension plate is provided to facilitate the construction of a more economical and stronger body able to withstand the forces imposed on the pipe capping apparatus during high pressure testing.

A plurality of cantilevered arms pivotally attached to the body are provided to axially center the pipe within the body. Drive means engage a drive surface upon the cantilevered arms to rotate the cantilevered arms. A handle serves as a means for actuating the drive means.

An improved attachment arrangement is provided to couple the jaw to the body. In particular, dual links are provided which result in a more stable linkage between the jaw and the body. Other arrangements for coupling the jaw to the body are also disclosed.

Example of the more important features of this invention have thus been summarized rather broadly in other that the detailed description thereof that follows may be better understood, and in order that the contributed to the art may be better appreciated. There are, of course, additional features of the invention that will be described hereinafter and which will also form the subject of the claims appended hereto. Other features of the present invention will become apparent with reference to the following detailed description of a presently preferred embodiment thereof in connection with the accompanying drawings, wherein like reference numerals have been applied to like elements, in which:

BRIEF DESCRIPTION OF THE DRAWINGS

Similar to FIG. 2, FIG. 4 shows a front view of an alternative embodiment of a jaw, jaw holder and arm.

FIG. 5 is a partialy cutaway side view of the embodiment depicted in FIG. 4.

FIG. 6 shows an elevation view of the pressure barrier apparatus depicting the lugs and interstices between the lugs.

FIG. 7 shows a cross-sectional view of the pressure barrier apparatus taken through section lines 7—7 in FIG. 6.

FIG. 8 shows a cross-sectional view of the pressure barrier apparatus for low pressure applications, the surface of the pipe, and the surface of the body.

FIG. 9 illustrates a cross-sectional view of an alternative embodiment of a pressure barrier apparatus for high pressure applications.

FIG. 9A illustrates an enlarged view of a portion of FIG. 9.

FIG. 10 is another view of the apparatus depicted in FIG. 9, showing the apparatus during pressurization.

FIGS. 10A and 10B illustrate enlarged views of portions of FIG. 10.

FIG. 11 and FIG. 12 show a cross-sectional elevational view of the ring illustrated in FIG. 9.

FIG. 12 shows a view of the ring illustrated in FIG. 11 during pressurization.

FIG. 13 and FIG. 14 illustrate an alternative embodiment of the ring depicted in FIG. 11 and FIG. 12, respectively.

FIG. 15 illustrates a cross-sectional elevational front view of the interface between the jaw tooth segment and the wall of the pipe.

Similar to FIG. 22.

FIG. 28 depicts a partially cut-away side view of an embodiment of the cylinder gripping apparatus employed as a safety hanging apparatus for a pipe.

FIG. 29 shows an enlarged side view of the force translation lug and the bearing groove in the body.

FIG. 30 illustrates a cut-away bottom view of the apparatus shown in FIG. 29.

FIG. 31 shows a partially cut-away bottom view of the apparatus illustrated in FIG. 28.

DETAILED DESCRIPTION OF A PREFERRED EMBODIMENT OF THE INVENTION

Figure 20:
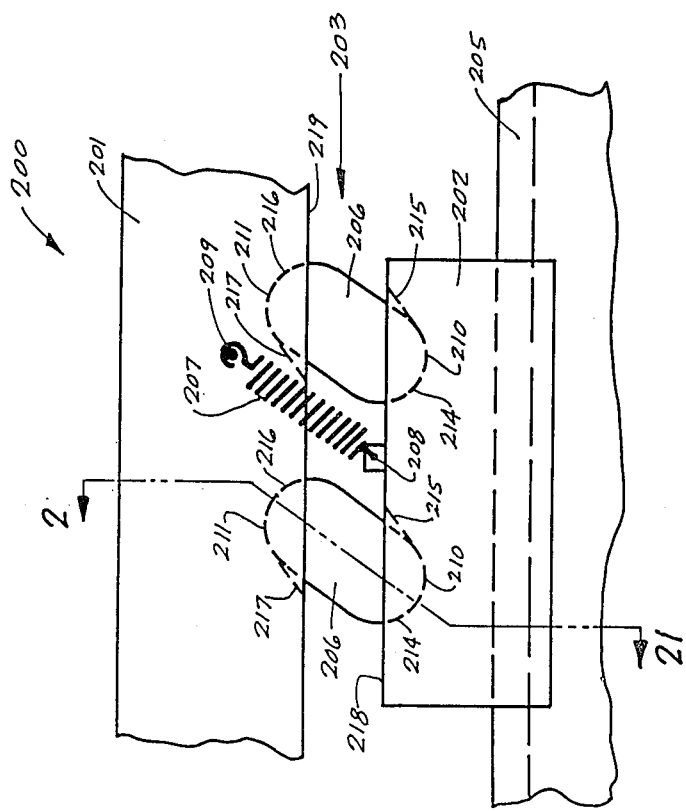
FIG. 20 depicts a side view of an embodiment of a cylinder gripping apparatus constructed in accordance with the present invention.

Turning now to the drawings in FIG. 20, there is depicted a side view of a portion of a cylinder gripping apparatus 200. The cylinder gripping apparatus 200 comprises a body 201, a jaw 202 and an interfacing assembly 203. The body 201 is only partially shown in FIG. 20.

Figure 21:
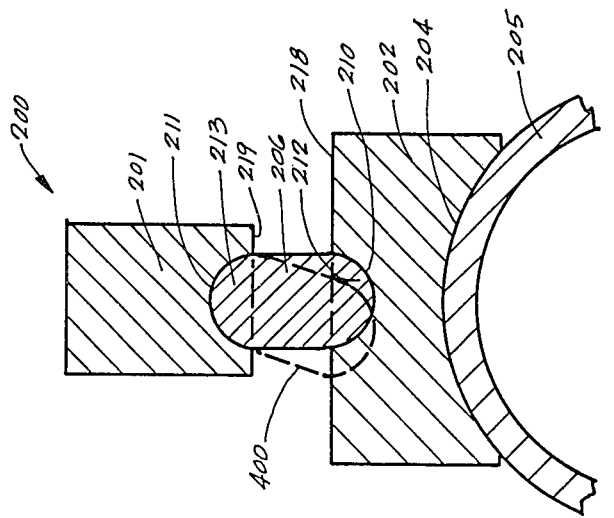
FIG. 21 shows a cut-away end view of the cylinder gripping apparatus depicted in FIG. 20.

As best shown in FIG. 21, the jaw 202 has a friction surface 204 adapted for gripping a cylinder 205. The friction surface 204 may comprises serrations, teeth, a smooth friction surface, or other conventional friction surfaces.

With reference to FIG. 20, the interfacing assembly 203 may comprise floating force translation lugs 206. The interfacing assembly also comprises a resilient member, elastic member or spring 207. The elastic member 207 is connected to the jaw 202 at a first spring anchor point 208. The elastic member 207 is connected to the body 201 at a second spring anchor point 209.

The floating force translation lugs 206 are floating in the sense that the lugs 206 are unconnected to either the body 201 or the jaw 202. The lugs 206 fit into first bearing grooves or sockets 210 formed in the jaw 202. The other end of the lugs 206 fit into second bearing grooves or sockets 211.

As shown in FIG. 21, the lug 206 has a first arcuate end or curved end 212 and a second arcuate or curved end 213. The first arcuate end 212 is adapted to fit into the first bearing groove 210. Similarly, the second arcuate end 213 is adapted to fit into the second bearing groove 211.

As best shown in the side view depicted in FIG. 20, the forced translation lugs 206 are angularly disposed between the body 201 and the jaw 202. The first bearing groove 210 has a first arcuate or curved bearing surface 214 which tapers to a sloped forward surface 215. The sloped forward surface 215 allows the lug 206 to rotate in a first sense inside the first bearing groove 210. In FIG. 20, the first sense of rotation is clockwise with respect to the jaw 202.

Similarly, the second bearing groove 211 comprises a second arcuate or curved bearing surface 216 which tapers to a sloped or planar rearward surface 217. The sloped reaward surface 217 permits the lug 206 to rotate in a first sense with respect to the body 201.

The lugs 206 are floating and thus unconnected to the body 201 or the jaw 202. Therefore, it is desirable to provide a means for compressively engaging the jaw 202 toward the body 211 in order to hold the lugs 206 within the first and second bearing grooves 210 and 211. In the present instance, this is eseentially accomplished by the elastic member 207. When the jaw 202 is not engaged against a cylinder 205, the elastic member 207 tends to urge the jaw 202 toward the body 201, thus holding the lugs 206 in engagement within the first and second bearing grooves 210 and 211.

It will be appreciated that some actuating means may be provided to urge the jaw 202 into initial engagement with the cylinder 205. When the jaw 202 is engaged against a cylinder 205 and an axial force urges the cylinder 205 in a forward direction, or to the right in FIG. 20, then the lugs 206 will tend to rotate in a second sense, or counterclockwise in FIG. 20. The tendency of the lugs 206 to rotate in a second sense will tend to urge the jaw 202 into gripping engagement with the cylinder 205. The gripping force between the jaw 202 and the cylinder 205 will be proportional to the axial force exerted upon the cylinder 205. Thus, the force translation lugs 206 provide a radial counterforce in response to the axial force upon the cylinder.

When the cylinder 205 is not perfectly axially aligned with respect to the body 201, it is desirable to permit the jaw 202 to move in a direction transverse to the axis of the body 201. As best shown in FIG. 21, it is desirable to allow the jaw 202 to move transversely, i.e., to the left or right, in order to allow the friction surface 204 to engage the cylinder 205. The curved ends 212 and 213 cooperate with the first opposing face 218 of the jaw 202 and the second opposing face 219 of the body 201 to permit a transverse displacement of the jaw 202 from an initial axially aligned position to a displaced position either to the right or to the left of FIG. 21. Thus, the floating lug 206 permits the friction surface 204 of the jaw 202 to engage the cylinder 205 even when the cylinder 205 is not perfectly axially aligned within the body 201.

Thus, the floating nature of the lug 206 which is interposed between the jaw 202 and the body 201 permits movement between the jaw 202 and the body 201 with at least three degrees of freedom. That is, the jaw 202 may move axially, radially and transversely with respect to the body 201. These degrees of freedom of movement that are permitted the jaw 202 with respect to the body 201 facilitate the effective engagement of the jaw 202 against the cylinder 205 even for imperfectly aligned cylinders 205.

In some applications, such as a wellhead snubber apparatus, it may be desirable to grip a pipe, tube or cylinder 205 to prevent rotation of the pipe, tube or cylinder 205 about the axis of the body 201. As shown in FIG. 21, the floating lug 206 may be positioned in offset position 400 (shown as a broken line). In the offset position 400, the lug 206 will tend to oppose clockwise rotation of the pipe 205. The gripping force of the jaw 202 upon the pipe 205 will be proportional to the clockwise torque upon the pipe 205. Similarly, counterclockwise rotation of the pipe 205 may be prevented by a jaw 202 with the lug 206 offset in an opposite direction, or to the right in FIG. 21 (not shown).

It will be appreciated that a second cylinder gripping apparatus 200 may be connected to the same pipe 205 as a first gripping apparatus 200 with a set of lugs 206 offset in an opposite direction in order to prevent both clockwise and counterclockwise rotation of the same pipe 205.

Figure 22:
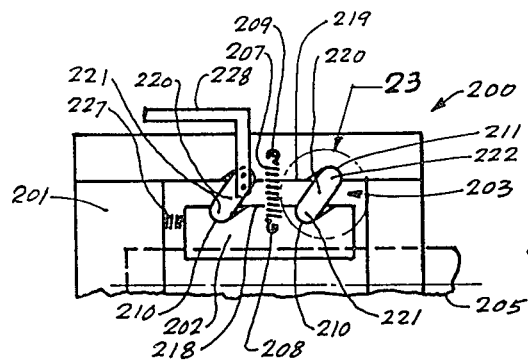
FIG. 22 shows a side view of an alternative embodiment of the cylinder gripping apparatus.
Figure 24:
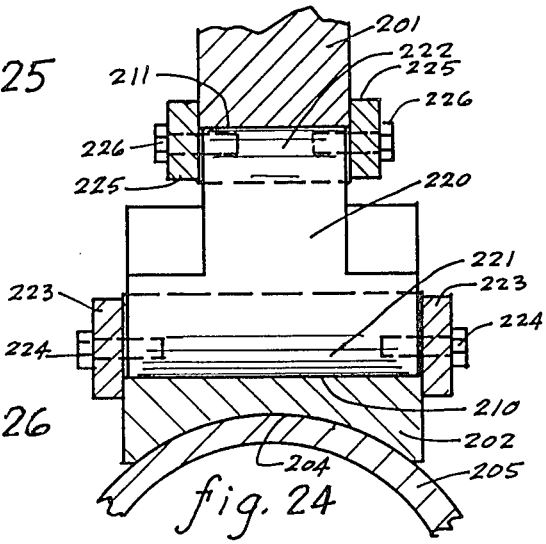
FIG. 24 illustrates a partially cut-away end view of the embodiment depicted in FIG. 23.

Turning now to FIG. 22, another embodiment of the interfacing assembly 203 is shown. The interfacing assembly 203 comprises floating lugs 220 interposed between the body 201 and the jaw 202. The floating lugs 220 may be fabricated differently from the lugs 206 illustrated in FIGS. 20 and 21. As best shown in FIG. 24, the lug 220 has a first curved or arcuate end 221 and a second curved or arcuate end 222. The first curved end 221 is wider than the second curved end 222. The first curved end 221 may be substantially the same width as the jaw 202. As best shown in FIG. 24, the first bearing groove 210 may extend across substantially the entire width of the jaw 202.

The first end 221 of the lug 220 may be held within the first bearing groove 210 by a set of first stays or retaining means 223. The first stays 223 are fixedly held against the jaw 202 by fastening means 224. Fastening means 224 may comprise a bolt, screw, pin, or other conventional fastening mechanisms.

Similarly, the second end 222 of the lug 220 may be held within the second bearing groove 211 by a set of second stays or retaining means 225. The second stays 225 are fixedly held against the body 201 by fastening means 226. Fastening means 226 may comprise a bolt, screw, pin, or other conventional fastening mechanisms.

Fastening means 224 and 226 are connected to the jaw 202 and the body 201, respectively. The first and second stays 223 and 225 are not connected to the lug 220. This can best be seen with reference to FIG. 23. The first and second stays 223 and 225 are adapted to cover at least a portion of the cross-sectional area of the first and second bearing surfaces or grooves 210 and 211 in the jaw 202 and the body 201, respectively. The first and second stays 223 and 225 are adapted to laterally retain the lug 220 within the first and second bearing grooves 210 and 211, while leaving the lugs 220 free to rotatively pivot within the bearing grooves 210 and 211.

The stays 223 and 225 may be omitted, as shown in FIG. 22, and are not essential for the operation of the cylinder gripping apparatus.

Thus, as shown in FIG. 22, the first and second curved ends 221 and 222 of the lug 220 cooperate with first and second opposing faces 218 and 219 of the jaw 202 and the body 201, respectively, to permit a transverse displacement of the cylinder 205 from an initial axially aligned position to a displaced position. This degree of freedom of movement of the jaw 202 in the transverse direction permits the jaw 202 to more evenly engage the cylinder 205 when the cylinder 205 is not perfectly axially aligned within the body 201.

As shown in FIG. 22, the opposing face 218 of the jaw 202 has a curved surface or bearing groove 210 adapted to receive the curved end 221 of the floating lug 220.

An elastic member 207 tends to urge the jaw 202 toward the body 201 in order to hold the lugs 220 into engagement within the first and second curved surfaces 210 and 211. A compression member or spring 227 tends to urge the jaw 202 into engagement with the cylinder 205. As shown in FIG. 22, the compression member 227 is interposed between the front of the body 201 and the jaw 202.

Actuating means 228 is connected to the lug 220 for rotationally pivoting the lug 220. Actuating means 228 may comprise a handle. Actuating means 228 may be used to rotationally pivot the lug 220 in a first sense, or clockwise as shown in FIG. 22, to permit the jaw 202 to disengage the cylinder 205.

It will be noted that the elastic member 207 tends to urge the jaw 202 radially outwardly with respect to the body 201, thus urging the lugs 220 into operative engagement with the first and second bearing grooves 210 and 211. When the cylinder 205 is removed from the body 201, the elastic member 207 tends to hold the jaw 202 and the body 201 into engagement with the lugs 220.

Figure 23:
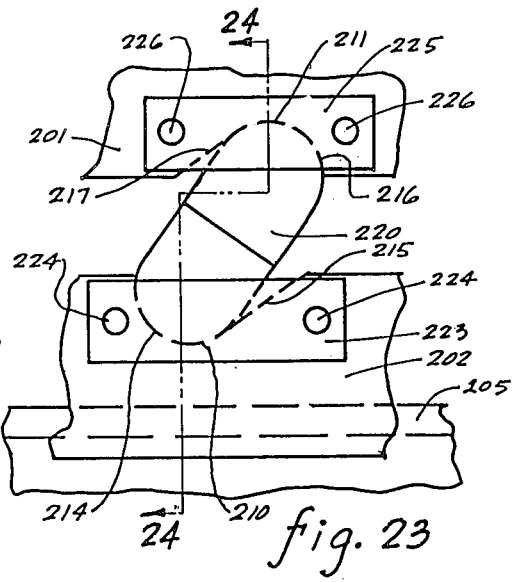
FIG. 23 shows a side view of the embodiment illustrated in FIG. 22 depicting the retainers or stays.

As shown in FIG. 23, the first bearing groove 210 comprises a first curved or arcuate bearing surface 214 which tapers to a sloped or planar forward surface 215. Similarly, the second bearing groove 211 comprises a second curved or arcuate bearing surface 216 which slopes to a planar or sloped rearward surface 217.

It will be appreciated that a floating force translatin by 206 may be constructed with a first arcuate, curved or spherical end 212 as shown in FIGS. 20 and 21, and with a second end fashioned in accordance with the embodiment described above with reference to FIGS. 22, 23 and 24.

Figure 25:
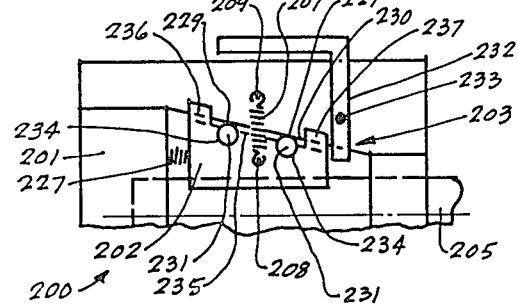
FIG. 25 is a side view of an alternative embodiment of the cylinder gripping apparatus.

Referring to FIG. 25, a side view of another embodiment of the present invention is illustrated. The interfacing assembly 203 is interposed between the sidewall of the body 201 and the jaw 202. In the present instance, the interfacing assembly 203 has curved or arcuate surfaces 229 which engage an opposing face 230 of the sidewall of the body 201. The curved or circular surfaces 229 form the outer surface of generally cylindrical or circular rollers 231. In a preferred embodiment, the rollers 231 are formed in the shape of cylindrical rods.

The rollers 231 are adapted to fit within channels 234 in the jaw 202. The channels 234 are formed transversely along the inner surface 235 of the jaw 202. As shown in FIG. 25, the inner surface 235 of the jaw 202 is inclined or sloped. Similarly, the opposing face 229 of the sidewall of the body 201 is similarly sloped or inclined.

The rollers 231 are floating, and are thus unconnected to either the jaw 202 or the body 201. The elastic member 207 tends to urge the jaw 202 radially outwardly toward the sidewall of the body 201. Thus, the elastic member 207 tends to hold the rollers 231 in the channels 234.

The rollers 231 facilitate the movement of the jaw 202 along the planar sloped opposing face 230 of the body 201. The rollers 231 are operable to facilitate the movement of the jaw 202 relative to the body 201 along the inclined inner surface 230.

The inclined inner surface 230 is adapted to urge the jaw 202 into engagement with the outer surface of the cylinder 205 when the jaw 202 is urged rearwardly, or to the right in FIG. 25, with respect to the body 201. A compression member, resilient member or spring 227 is adapted to urge the jaw 202 rearwardly with respect to the body 201.

Actuating means 232 is pivotally connected to the body 201 at a pivot point 233. Actuating means 232 may comprise a handle, in a preferred embodiment. Actuating means 232 is adapted to urge the jaw 202 generally forwardly, but that is to the left in FIG. 25, with respect to the body 201. Thus, actuating means 232 may be used to disengage the jaw 202 from the cylinder 205.

The rollers 231 may be confined to the channels 234 by stays 225 (not shown).

Because the rollers 231 are floating, the jaw 202 is permitted to move transversely with respect to the body 201. This transverse movement of the jaw 202 permits the jaw to grip the cylinder 205 even when the cylinder 205 is not axially centered within the body 201. Thus, the curved surface of the rollers 231 is cooperable with the opposing face 230 of the body 201 to permit a transverse displacement of the jaw 202 from an initial axially aligned positioned to a displaced position.

It will be appreciated that the channels 234 are preferably generally cylindrically shaped in substantial correspondence with the shape of the rollers 231. A first boss, finger or projection 236 limits the transverse movement of the jaw 202 with respect to the body 201. The boss 236 prevents the jaw 202 from completely slipping out of the cylinder gripping apparatus 200. Similarly, a second boss, finger or projection 237 is formed upon the rear of the jaw 202.

Figure 26:
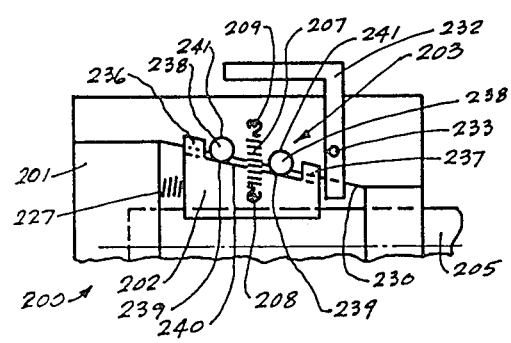
FIG. 26 is a side view of yet another alternative embodiment of the cylinder gripping apparatus.

FIG. 26 illustrates an alternative embodiment of the interfacing assembly 203 interposed between the jaw 202 and the body 201.

In the present instance, generally cylindrical roller 238 have curved, arcuate or generally round surfaces 239 which are cooperable with an opposing planer inclined face 240 of the jaw 202 to permit movement of the jaw 202 with respect to the body 201. The rollers 238 fit within generally cylindrically shaped channels 241 formed transversely along the inclined or sloped inner surface 230 of the side wall of the body 201. The rollers 238 permit the jaw 202 to move transversely with respect to the body 201 in a manner similar to the interfacing assembly described with reference to FIG. 25.

In other respects the interfacing assembly 203 depicted in FIG. 26 is constructed and operated similar to the interfacing assembly 203 described with reference to FIG. 25.

Figure 27:
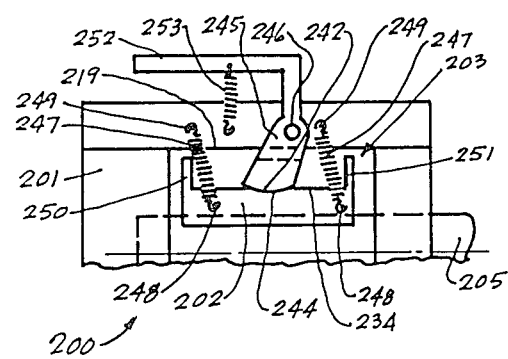
FIG. 27 illustrates a side view of an alternative embodiment of the cylinder gripping apparatus.

Turning now to FIG. 27, the interfacing assembly 203 is interposed between the body 201 and the jaw 202. In the present instance, the interfacing assembly 203 has a curved surface 242 which interfaces with an opposing face 243 of the jaw 202. The opposing face 234 of the jaw 202 is located generally opposite to the friction surface 204 of the jaw 202.

The opposing face 234 of the jaw 202 has a curved surface or groove 244 formed in a position generally in correspondence with the curved surface 242 of the interfacing assembly 203. The curved surface 242 of the interfacing assembly 203 is cooperable with the opposing face 234 of the jaw 202 to permit the jaw 202 to move not only radially and axially with respect to the body 201, but also transversely with respect to the body 201. Thus, if the cylinder 205 is not axially centered within the body 201, the curved surface 242 will permit the jaw 202 to move from an initial axially centered position to a displaced position in correspondence with the uncentered or displaced position of the cylinder 205. Thus, the interfacing assembly 203 permits the jaw 202 to be displaced transversely with respect to the body 201 in order to more effectively engage the cylinder 205 when the cylinder 205 is deformed or uncentered within the body 201.

The interfacing assembly 203 further comprises a cam arm or force translation arm 245 which may be pivotally connected to the body 201 at a second pivot point 246. The cam arm 245 is operable to urge the jaw 202 into engagement with the outer surface of the cylinder 205 when the cam arm 245 is rotated in a second sense, or counterclockwise in FIG. 27, with respect to the body 201.

Elastic members or springs 247 are connected to the jaw 202 at first spring anchor points 248 and are connected to the body 201 at second spring anchor points 249. The elastic members 247 tend to urge the jaw 202 radially outwardly with respect to the body 201. Thus, the elastic members 247 tend to urge the jaw 202 into engagement with the generally arcuate cam surface 242 of the cam arm 245.

In the present instance the jaw 202 has a forward alignment lip 250 and a rear alignment lip 251. The alignment lips 250 and 251 are connected to the forward and rear edges of the jaw 202 respectively, as shown in FIG. 27. The alignment lips 250 and 251 operate to disengage the entire jaw 202 from the cylinder 205 in the event that either the forward or rear end of the jaw 202 does not initially disengage from the cylinder 205. If the cam arm 245 is rotated in a first sense, or clockwise in FIG. 27, with respect to the body 201, the jaw 202 will be urged radially outwardly from the cylinder 205 by the elastic members 247. In the event that the rear portion of the jaw 202 does not initially disengage from the cylinder 205, the forward alignment lip 250 will contact the inner surface 219 of the body 201. Thus, further rotation of the cam arm 245 in a first sense with respect to the body 201 will cause the jaw 202 to pivot about the point where the forward alignment lip 250 contacts the inner surface 219 of the body 201 and will cause the rear portion of the jaw 202 to disengage from the cylinder 205.

In the present invention, the cam arm 245 has actuation means or a handle 252 connected to it. An elastic member or spring 253 may be connected between the handle 252 and the body 201. The elastic member 253 will tend to urge the cam arm 245 to rotate in a second sense with respect to the body 201 and thus urge the jaw 202 into engagement with the cylinder 205.

It will be appreciated that the interfacing assemblies 203 illustrated in FIGS. 22, 25, 26 and 27 are adapted to provide a radial counterforce in response to an axial force upon the cylinder. If an axial force is exerted upon the cylinder 205 when the jaw 202 is in engagement with the cylinder 205, and the cylinder 205 is urged to the right in FIGS. 22, 25, 26 and 27, the interfacing assemblies 203 will provide a radial counterforce or gripping force which is proportional to the axial force exerted upon the cylinder 205.

It will also be appreciated that, similar to FIG. 27, the interfacing assembly 203 illustrated in FIGS. 20, 21, 22, 23 and 24 may be pivotally connected at one end to either the jaw 202 or the body 201.

In FIG. 28, an embodiment of the present cylinder gripping apparatus is shown for use in connection with a safety hanger or blowout preventer apparatus for use in connection with drilling operations. The embodiment illustrated in FIG. 28 may also have utility as a snubber.

As illustrated in FIG. 28, the body 201 has an upper cylinder, pipe or tube passageway or opening 254 and a lower pipe, tube or cylinder passageway or opening 255. The body 201 is adapted to axially receive the pipe, tube or cylinder 205. The jaws 202 have a friction surface 204 adapted to grip the drill pipe 205.

In the present instance, the interfacing assembly 203 comprises angularly disposed floating force translation lugs or arms 256. The lug 256 is floating because it is unconnected to the body 201 or the jaw 202. The lug 256 has a first curve surface or arcuate surface 257 on one end and a second curved or arcuate surface 258 on the other end. The first curved end 257 is adapted to fit within a first bearing groove 259. Similarly, the second curved end 258 is adapted to fit within a second bearing groove 260. The bearing grooves 259 and 260 are constructed similar to the bearing grooves 211 and 214 illustrated in FIGS. 22, 23 and 24. For example, as best shown in FIG. 29, the second bearing groove 260 comprises a second curved or arcuate bearing surface 261 which tapers to a generally planar or inclined surface 262.

As best shown in FIG. 29, the lug 256 is floating in the sense that it is not connected to the body 201. First and second retaining means or stays 265 and 266 are connected or fastened to the jaw 202 and the body 201 respectively. The stays 265 and 266 retain the lugs 256 when the pipe 205 is withdrawn from the body 201, as will be more fully described below.

Referring to FIG. 29, the stay 266 has an aperature or opening 263. The aperture 263 is adapted to receive a projection or pin 264 connected to the lug 256. As best shown in FIG. 30, the pin 264 is connected to the lug 256 and extends through the aperture 263 in the stay 266. When the jaw 202 engages the pipe 205, the lug 256 engages the grooves 259 and 260. When the lug 256 is engaged with the grooves 259 and 260, the pin 264 does not contact the stay 266. As best shown in FIG. 29, the aperture 263 is larger than the pin 264. Thus, the lug 256 is essentially floating. The pin 264 cooperates with the stay 266 to retain the lug 256 when the pipe 205 is withdrawn from the body 201.

As best shown in FIGS. 29 and 30, the stay 266 is connected to the body 201 by fastening means 267. Fastening means 267 may comprise a bolt, screw, pin or other conventional fastening mechanisms. Referring to FIG. 28, the first stay 265 is similarly connected to the jaw 202. In addition, the lug 256 has a corresponding pin 268 which is adapted to fit within an aperture in the first stay 265. It will be appreciated that either end of the lug 256 may be pivotally connected to the body 201 or jaw 202.

The operation of the interfacing assembly 203 illustrated in FIGS. 28 through 31 and providing a radial counterforce or gripping force upon the pipe 205 in response to an axial force upon the pipe 205 is similar to the interfacing assemblies 203 described above with reference to FIGS. 20 through 27.

The interfacing assembly 203 illustrated in FIG. 28 further comprises a jaw housing 269. The jaw housing 269 has arm passage openings 270 which permit the lugs 256 to pass through the jaw housing 269. A compression member or spring 271 is provided between the body 201 and the jaw housing 269. The spring 271 tends to urge the jaw housing 269 downward as shown in FIG. 28. This tends to urge the jaws 202 into engagement with the pipe 205.

A wiper 272 is provided to remove dirt, grime and other foreign matter from the surface of the pipe 205. The wiper 272 operates to prevent dirt and other matter upon the surface of the pipe 205 from interfering with the gripping surface 204 of the jaws 202.

A releaser, jaw releasing cylinder or cylinder means 273 is connected to the body 201. The releaser 273 has a rod 274 shown in FIG. 28 in the retracted position. The rod 274 is operable to be extended from the releaser 273 so that it contacts the jaw housing 269 and urges it upward. The releaser 273 is adapted to compress the spring 271 and thus disengage the jaw 202 from the pipe 205.

It will be appreciated that a second similar body 275 may be stacked with the body 201 to provide more than one set of jaws 202 to grip the pipe 205. The pipe 205 is shown in FIG. 28 with a casing 276. A second set of jaws provided in the second body 275 would operate to grip the pipe 205 when the casing 276 was passed through the body 201.

Employed as a safety hanger apparatus, the embodiment of the invention illustrated in FIG. 28 would permit the drill pipe 205 to be removed from the hole by moving it upward. However, if the drill pipe 205 was dropped, the jaws 202 would automatically engage the drill pie 205 and prevent it from falling into the hole (not shown). The jaws 202 are adapted to permit the drill pipe 205 to be moved upwardly in FIG. 28, and are adapted to prevent the drill pipe 205 from being dropped down the hole or for moving downwardly in FIG. 28.

It will be appreciated that the embodiment of the invention illustrated in FIG. 28 may have useful application for other types of pipe, tubes or cylinders. The present invention is not intended to be limited to drill pipe.

In the event that it is desired to drill and move the drill pipe 205 downwardly, a similar body 201 may be employed as a blowout preventer by turning the body 201 upside down from the position shown in FIG. 28. In such a position, the jaws would permit the drill pipe 205 to be drilled down into the hole, but would not allow the drill pipe 205 to be blown out of the hole even in the event of a sudden increase in downhole pressure. The gripping force of the jaws 202 upon the drill pipe 205 will be proportional to the downhole pressure. Thus, the gripping force of the jaws 202 upon the drill pipe 205 will increase in proportion to any increases in the downhole pressure. Thus, a great safety feature is achieved by the present invention because a sudden increase in downhole pressure will be immediately offset by an increase in the radial counterforce or gripping force of the jaws 202 upon the drill pipe 205.

The releaser 273 is operable to disengage the jaws 202 when it is desired to move the drill pipe 205 in a direction opposite to the direction of movement permitted by the jaws 202.

Figure 32:
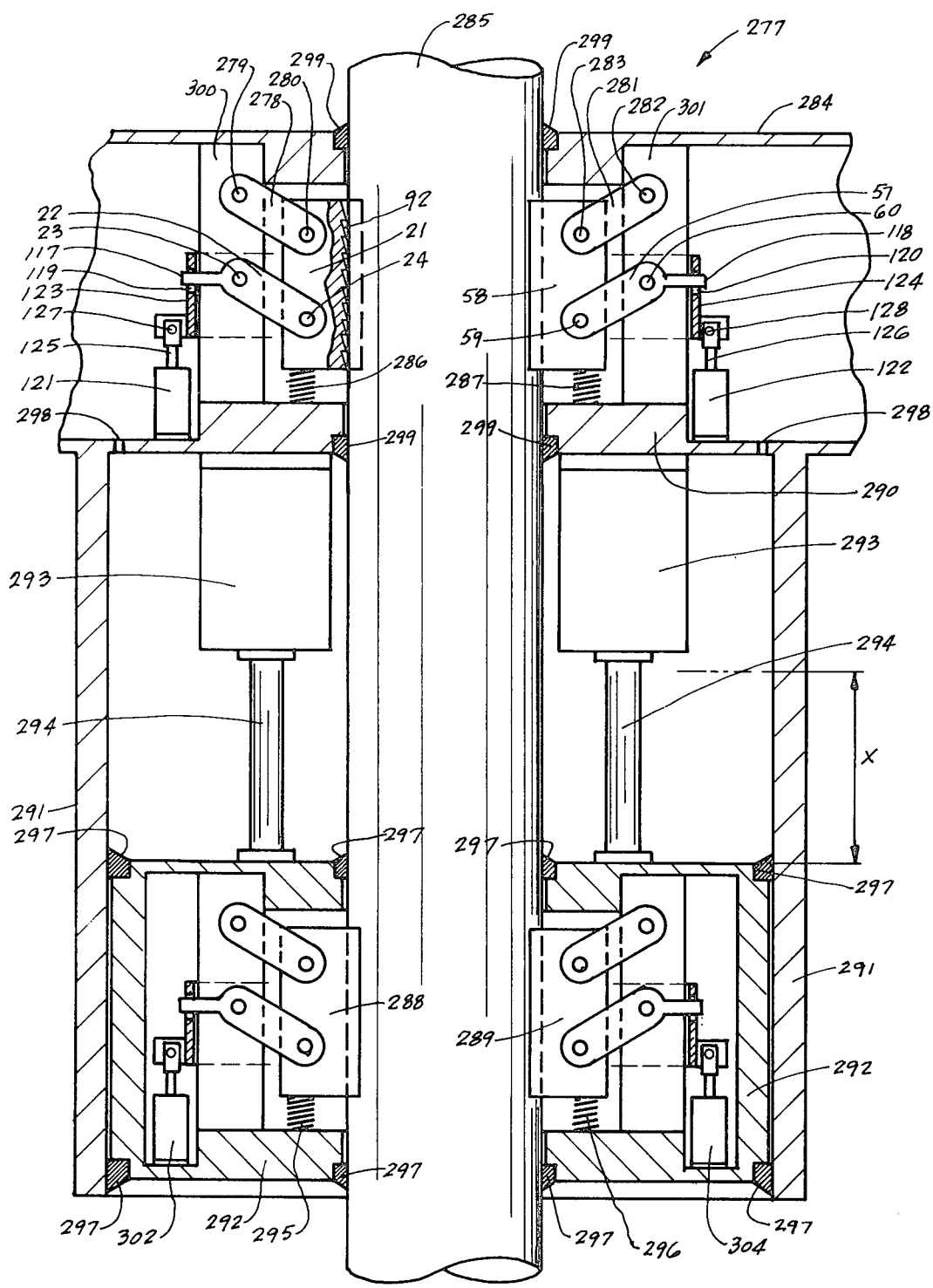
FIG. 32 depicts an embodiment of the cylinder gripping apparatus employed as a drilling platform jacking apparatus.

FIG. 32 depicts an embodiment of the cylinder gripping apparatus having utility as an offshore drilling platform deck jacking apparatus.

Although any of the interfacing assemblies previously described with reference to FIGS. 20 through 31 may be used to interface jaws with a body, the illustrated embodiment of the platform jacking apparatus 277 comprises a first jaw 21, a fist arm 22, a first pivot point 23, a second pivot point 24, a first extension 117, a first guide or synch sleeve 123, a first shoe or fastening means 119, a first actuation means 121, a first shaft 125 and a first fastening means 127, as are described more fully with respect to FIGS. 18 and 19 in the application for a hydrostatic testing apparatus, Application Ser. No. 037,140, filed May 8, 1979, by the same applicant, which is incorporated herein by reference.

Similarly, a second jaw 58, second arm 57, third pivot point 60, fourth pivot point 59, second extension 118, second guide or synch sleeve 124, second shoe 120, second actuation means 122, second shaft 126 and second fastening means 128 operate in a manner similar to the corresponding elements illustrated and described with reference to FIGS. 18 and 19 of Application Ser. No. 037,140, filed May 8, 1979, for a hydrostatic testing apparatus, by the same applicant, which is incorporated herein by reference.

In the embodiment shown in FIG. 32, a third arm 278 is pivotally connected to the body at a fifth pivot point 279. The third arm 278 is pivotally connected to the first jaw 21 at a sixth pivot point 280. A fourth arm 281 is pivotally connected to the body 290 at an eighth pivot point 282. The fourth arm 281 is connected to the second jaw 58 at an eighth pivot point 283. The body 290 is connected to a platform 284 in the present instance, the platform 284 comprises a conventional offshore drilling platform. The first and second jaws 21 and 58 comprise a first set of jaws which are adapted to grip a platform leg 285. A first compression member or spring 286 is interposed between the first jaw 21 and the body 290. The spring 286 is adapted to urge the first jaw 21 into engagement with the platform leg 285. A second compression member or spring 287 similarly urges the second jaw 58 into engagement with the platform leg 285. A third jaw 288 and a fourth jaw 289 comprise a second set of jaws adapted to grip the platform leg 285. The second set of jaws 288 and 289 operate in a manner similar to the first set of jaws 21 and 58. The body 290 has a guide sleeve 291 which is adapted to receive a jaw housing 292 which is annularly shaped as shown in FIG. 32. The jaw housing 292 is adapted to axially receive the platform leg 285. The body 290 is similarly adapted to axially receive the platform leg 285. The jaw housing 292 is adapted to reciprocally slide within the guide sleeve 291 of the body 290. Actuation means or cylinder means 293 is connected to the body 290. Actuation means 293 has a shaft 294 which is operable to reciprocally extend or retract within actuation means 293. The shaft 294 is connected to the jaw housing 292.

The platform 284 may be jacked up the platform leg 285 by allowing the second set of jaws 288 and 289 to engage the platform leg 285 while the shafts 294 are in the retracted position. When the shafts 294 are in the retracted position, the jaw housing 292 will be retracted within the guide sleeve 291 of the body 290. Thus, cylinder means 293 may be used to extend shafts 294 to push the jaw housing 292 downwardly with respect to the body 290. Thus, the body 290 and the platform 284 are raised with respect to the platform leg 285 while the jaw housing 292 remains stationary with respect to the platform leg 285.

In FIG. 32, the shaft 294 is shown in the fully extended position. The shaft may be extended a distance X as shown in FIG. 32. Thus, for each motion, the platform 284 may be jacked up a distance X.

When the shaft 294 has reached the fully extended position, the first set of jaws 21 and 58 are allowed to engage the platform leg 285. Thus, the first set of jaws 21 and 58 will hold the platform 284 in position as the shafts 294 and the second set of jaws 288 and 289 are retracted within the guide sleeve 291. It will be appreciated that both the first set of jaws 21 and 58 and the second set of jaws 288 and 289 will permit the platform leg 285 to be moved in one direction with respect to the body 290 and the jaw housing 292, but will not permit the platform leg 285 to be moved in an opposite direction with respect to the body 290 or the jaw housing 292.

The first and second springs 286 and 287 are adapted to insure that the first set of jaws are urged generally radially inwardly with sufficient force to insure that the first set of jaws 21 and 58 maintain contact with the platform leg 285. Thus, if the second set of jaws 288 and 289 should fail for any reason, the first set of jaws 21 and 58 would automatically grip the platform leg 285 with a gripping force proportional to the weight of the platform 284 or proportional to the stresses upon the platform leg 285. Similarly, a third and fourth spring or compression member 295 and 296 urge the second set of jaws 288 and 289 into engagement with the platform leg 285.

In the present instance, a plurality of wipers 297 is provided between the jaw housing 292 and the guide sleeve 291 and the platform leg 285. The wipers 297 tend to keep sea water or other unwanted matter from contaminating the interior of the guide sleeve 291. Air vent ports 298 provide fluid communication between the air within the interior of the guide sleeve 291 and the external atmosphere.

A plurality of second wipers 299 is provided between the body 290 and the platform leg 285.

In the illustrated embodiment, the first and third arms 22 and 278 are pivotally connected to a first spline or rib 300 formed from the body 290. Similarly, the second and fourth arms 57 and 281 may be pivotally connected to a second spline or rib 301 formed from the body 290.

The actuation means 121 and 122 may also comprise a first releasor operable to release the first set of jaws 21 and 58 from engagement with the platform leg 285. Similarly, actuation means 302 and 304 may comprise a second releasor operable to release the second set of jaws 288 and 289 from engagement with the platform leg 285. The second releasor 302 and 304 is operable to disengage the second set of jaws 288 and 289 to permit the retraction of the jaw housing 292 within the guide sleeve 291.

The platform 284 may be lowered, also by synchronized operation of first and second releasers 121 and 122, and 302 and 304, in a manner generally opposite to that described above with reference to jacking the platform 284 up.

It will be appreciated that the cylinder gripping apparatus described above may find utility in any application where it is desirable to grip a cylinder, rod pipe or tube to keep the cylinder, rod pipe or tube from going in an unwanted direction. The cylinder gripping apparatus may be employed with utility to hold the end of a pipe to be forged during the process of upsetting tubing. Alternatively, the cylinder gripping apparatus may find utility in holding tubing during the process of belling where a mandrel is inserted and welded to a pipe or tube. Similarly, any operation that requires a pipe, tube or cylinder to be held or gripped where large axial forces tend to urge the pipe, tube or cylinder in an unwanted direction.

Figure 1:
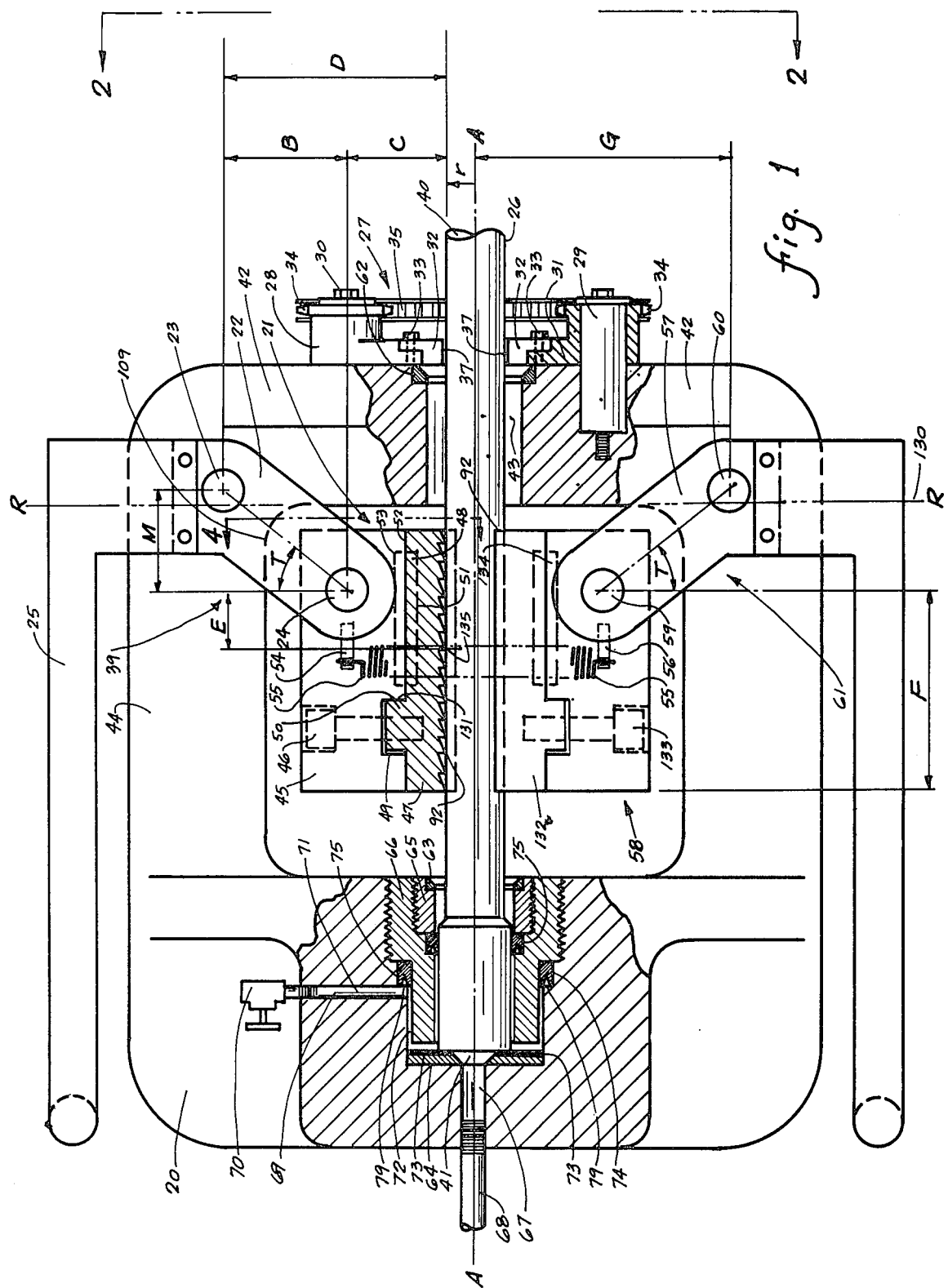
FIG. 1 depicts a partial cutaway side view of an embodiment of a pipe capping apparatus constructed in accordance with the present invention.

Turning first to FIG. 1, there is shown a partial cutaway view of a pipe capping apparatus 19 according to the present invention. In a preferred embodiment, a body 20 and a jaw assembly or jaw 21 are coupled together with a radial force translator 39. The radial force translator 39 transforms the axial force exerted upon the body 20 by a fluid introduced into the interior region 40 of a pipe 26 to a force radially inwardly. The pressure from the fluid is applied to the body 20 generally in an interior zone 41 within the body 20. The radial force translator 39 transforms this axial force into a radially inward force, or a radial counterforce, which is applied to the outer walls of the pipe 26 by the jaws 21. This radial counterforce must be sufficient to hold the pipe during pressurization. Pursuant to the invention, the radial counterforce is always larger and proportional to the axial force upon the body 20 to assure that the apparatus 19 will not be forced off of the pipe 26 during pressurization. Thus, when no pressure is exerted upon the fluid within the pipe 26, little force will be exerted against the outer surface of the pipe 26 by the jaws 21. As a safety feature, the greater the pressure upon the inside 40 of the pipe 26, the greater the gripping force exerted by the jaws 21 upon the outer surface of the pipe 26.

In a preferred embodiment, the radial force translator 39 comprises an arm 22 pivotally disposed against or connected to the body 20 at a first pivot point or pin 23. The arm 22 is also connected to the jaw 21 at a second pivot point or pin 24. The first pivot point 23 and the second pivot point 24 are adapted to permit the arm 22 to rotate. Rotation of the arm 22 permits the jaw or jaw assemnbly 21 move into and out of engagement with the surface of the pipe 26.

The radial translator 39 transforms the axial force into a radial counterforce proportional to the tangent of a translation angle T. Different translation angles T may be selected to give the desired amount of radial counterforce. The translation angle T will depend upon the length of the arm 22, measured between the first pivot point 23 and the second pivot point 24, and the distance of the first and second 23 and 24 from the outer wall of the pipe.

The radial counterfore will always be proportionally related to the axial pressure force. The axial pressure force will be substantially equal to the internal fluid pressure multiplied times the cross-sectional area of the pipe 26. The radial force translator 39 is operable to produce a radial counterforce applied by the jaws 21 to the pipe 26 which is proportional to the pressure multiplied times the cross-sectional area of the pipe 26, all divided by the tangent of the translation angle T.

It is contemplated that the translation angle T may be an angle anywhere between 10° and 45°. It has been found that a preferred embodiment of the radial force translator 39 employs a translation angle T between 30° and 40°. In the practice of a preferred embodiment, it has been found that a translation angle T of 37° provides satisfactory results.

The translation angle T is determined by a jaw face offset C, a length of the arm 22 measured between the center of the first pivot point 23 and the center of the second pivot point 24, and an arm offset D. In a preferred embodiment, the location of the first pivot point 23 should be chosen such that it is located in a tension member 42 of the body 20. The diameter of the pipe 26 to be tested will also be known.

The strength of the material composing the jaw 21 is important in determining the jaw face offset C. The pin 24 is preferably located as close to the pipe 26 as possible consistant with required clearances and allowable stresses. In a preferred embodiment where the jaw 21 comprises a single member, the jaw face offset C is substantially equal to a distance of 2 or 2½ diameters of a pin inserted into the second pivot point 24. In a preferred embodiment, the jaw 21 may be fabricated from steel, or more specifically heat-treated steel. In the practice of a preferred embodiment, it has been found that highly ductle carbuerized steel (AISI 1040 or 8620) provides satisfactory results for the jaw tooth segment 47. The teeth surface should preferably be case hardened to Rockwell C-50 or C-60.

Generally, it has been found that the allowable shear stress upon the pin 24, and also the pin 23, should not exceed 25% of the ultimate yield of the steel composing the pins 24 or 23.

The radial force or clamping force should be greater than the axial pressure force exerted upon the body 20. The axial force is substantially equal to the pressure of the fluid in the inner zone 41 of the body 20 times the cross-sectional area of the pipe 26. The radial force is equal to the axial force divided by the tangent of the transformation angle T.

Referring to FIG. 1, it is desirable to have the second pivot point 24 located upon the jaw assembly 21 such that the tendency of the front teeth 92 to bite into the pipe 26 with more force than the other teeth 92 is minimized. It is desirable to evenly distribute the radial gripping force exerted by the jaw 21 upon the pipe 26 evenly over the area of the jaw 21 in contact with the surface of the pipe 26.

In practice, it has been found desirable to place the second pivot point 24 to the rear of the jaw holder 45 of the jaw assembly 21, or in the case of a single member jaw 21, to the rear of the jaw 21. This reduces the tendency of the front teeth 92 to bite into the surface of the pipe 26.

Useful results may be obtained by placing the second pivot point 24 generally in the center of the rear one-half of the jaw 21.

More specifically, in a preferred embodiment, the second pivot point 24 should be connected to the rear portion of the jaw 21 a distance F (shown in FIG. 1) from the front of the jaw 21 which is sufficient to minimize the tendancy of the front teeth 92 to overbite into the pipe 26 and to mar, deform or leave excessive teeth imprints in the surface of the pipe 26. In practice, the second pivot point 24 may be connected a distance F from the front of the jaw 21 which is equal to the jaw face offset C multiplied times the crosssection area of the pipe 26 multiplied times the maximum test pressure that will be desired, all divided by a pipe stress factor. In practice, a pipe stress factor of 2,000 has been found to provide satisfactory results. It will be appreciated that the pipe stress factor may be less than 2,000. This factor is based upon the amount of pressure that may be exerted by the front teeth 92 of the jaw 21 upon the pipe 26. The pipe stress factor 2,000 is based upon a permissible radially inwardly force upon the front teeth 92 and may be defined as 2,000 pounds per inch upon the front jaw surface circumferentially contacting the surface of the pipe 26. It will be appreciated that the pipe stress factor is a function of the maximum test pressure desired and the jaw face offset C.

As discussed above, the jaw face offset C is made as small as possible consistent with the amount of clearance required to prevent movement of the jaw 21, and consistent with the allowable stresses that may be withstood by the jaw 21 such that the pin 24 does not overstress the portion of the jaw 21 between the pin 24 and the pipe 26.

The location of the second pivot point 24 may alternatively be established where the second pivot point 24 is placed a distance F from the front of the jaw 21 equal to the jaw face offset C multiplied times the maximum test pressure desired divided by the circumference of the pipe 26 to be tested and divided by the force stress factor. In practice, a force stress factor of 2,000 lbs. per inch has given satisfactory results.

It is desirable, in locating the second pivot point 24 upon the jaw 21, to minimze the difference between the moments about the center 135 of the friction surface 92 of the jaw 21 in contact with the pipe 26. Thus, the jaw face offset C times the axial force that will be axially asserted by the pipe 26 against the teeth 92 at the pressure to be tested should equal to a load centerline distance E measured axially between the center 135 of the jaw face 92 and the second pivot point 24 times the radial force that will be asserted radially inwardly at the center 135 of the jaw 21 against the pipe 26. Thus, the centerline distance E between the second pivot point 24 and the center of the jaw face 92 should be equal to the jaw face offset C times the axial force divided by the radial force.

It will be appreciated that the axial force will be substantially equal to the cross-sectional area of the pipe 26 times the test pressure. The radial force substantially equals the axial force multiplied by the cotangent of the translation angle T. It will be appreciated that the desired test pressure and the size of the pipe to be tested will be known.

Referring to FIG. 1, the ratio of the radial force exerted radially inwardly by the jaw 21 against the pipe 26 to the test pressure multiplied times the cross-sectional area of the pipe 26, should equal the ratio of the distance D measured between the first pivot point 23 and the surface of the pipe 26 minus the jaw face offset C all divided by the distance M measured axially between the first pivot point 23 and the second pivot point 24.

It is desirable to have the radial gripping force exerted by the jaw 21 against the pipe 26 be larger than the axial force tending to urge the apparatus 19 off of the pipe 26. In a preferred embodiment, the radial gripping force should range from a force substantially equal to the axial force, to a force as much as fifty percent greater than the axial force. In practice, an embodiment that achieves a radial gripping force substantially equal to one hundred and thirty-five percent of the axial force has been found to give satisfactory results. It will be appreciated that the magnitude of the desirable radial gripping force is related to the coefficient of friction between the jaw surface 92 and the pipe 26. The lower the coefficient of the pipe 26 is, the more radial gripping force required.

The area of the jaw 21 in contact with the surface of the pipe 26 is preferably such that the mechanical pressure per square inch on the outer wall of the pipe 26 is substantially equal to or larger than the fluid pressure per square inch on the inner wall of the pipe 26, as illustrated in FIG. 15. The area of the second jaw 58 is similarly determined.

In practice, satisfactory results have been obtained where the second pivot point or pin 24 is located one pin diameter below the top surface of the jaw 21, where the top surface of the jaw 21 is the surface generally opposite the friction surface 92. Satisfactory results have been obtained where the second pivot point 24 is located one and a half to three pin diameters from the rear of the jaw 21; however, the distance to the rear (or to the right of pin 24 in FIG. 1) of the jaw 21 is not significantly important. The important feature in locating pin 24 is how far the pin 24 is located from the front of the jaw 24.

The body 20 has a tension member 42 formed at the rear zone or rear of the body 20, shown in FIG. 1 as the region 130 to the right of the broken line R-R. The first pivot point 23 is located to the rear 130 of the body 20 such that the first pivot point 23 is located radially in line with the tension member 42. This arrangement of the first pivot point 23 and the tension member 42 provides a superior advantage in the force bearing properties of the body 20.

When pressurized fluid is introduced into the interior zone 40 of the pipe 26, the apparatus 19 is urged off of the pipe 26, or to the left in FIG. 1. This urging force is transmitted through the radial force translator and tends to urge the first pivot point 23 radially outwardly. The tension member 42 comprises a member or plate having an aperture 43 adapted to receive the pipe 26. The tension member 42 bears the tension force created by the first pivot point 23 and bears the stress that would otherwise be transmitted to the front of the body and greatly magnified by the leverage action of a side 44 of the body 20.

Without the tension member 42, the first pivot point 23 would urge radially outwardly upon the side 44. The side 44 would act like a lever to magnify the strength of this force upon the front of the body 20. Under high pressure testing, the force upon the rib shown in the earlier patent 4,077,250 could be great enough to fracture the body 20, resulting in the destruction of the hydrostatic testing apparatus. Without the tension member 42, a large and relatively expensive side 44 of the body 20 would be required to withstand high pressure testing.

In a preferred embodiment, the body 20 is formed or joined integrally with the tension member 42 such that the body 20 is formed into a one piece member including the tension member 42 and the side 44. The tension member 42 redistributes the stress created by the force exerted upon the first pivot point 23. This force is born directly in tension by the tension member 42. This results in a more practical, and more economically constructed, embodiment.

In an alternative embodiment, the tension member 42 may comprise a separate plate securely fastened to the body. In such an embodiment, the tension plate 42 should have overlapping lips or a collet located radially outwardly from the body 20 to hold the side 44 of the body 20 radially inwardly if the first pivot point 23 is located in the body 20. Conventional fastening means could be used to attach the plate 42 to the body 20.

It is desirble to permit the same testing apparatus 19 to test a variety of pipe sizes. It is also desirable to permit the apparatus 19 to test a pipe 26 with an upset, bell end or coupling end. The pipe receiving aperture 43 must be large enough to pass the upset, bell end or coupling. Thus, some means is required to axially center the pipe 26 within the body 20.

Referring to FIG. 1, a centralizer 27 is connected to the rear of the body 20 at the tension plate 42. The centralizer 27 is adapted to axially center the pipe 26 to be hydrostatically tested. The centralizer 27 comprises a plurality of rotatable cam levers or cantilevered arms 28. The cam levers 28 have a cam piece 32 adapted to urge the pipe 26 into an axially centered position within the pipe receiving zone or aperture 43 of the body 20 or the tension member 42. The cam lever 28 is joined to the cam piece 32 by fastening means 33 comprising a bolt, screw or a pin. In a preferred embodiment, fastening means 33 is adapted to permit removal of the cam piece 32. Therefore, the cam piece 32 may be changed for various sizes of pipe in order to permit the adaptability of the centralizer 27 to varying outside diameters of pipe.

The cam lever 28 is rotatably attached to the tension member 42 by fastening means 30 and 29. Fastening means 30 may comprise a screw or bolt and fastening means 29 may comprise a cylinder or a pin.

The cam lever 28 may comprise a cantilevered arm 31 pivotally attached to the body 20 by means of a pivot cylinder 29 fastened to the body 20 with a bolt 30. The cam lever 28 has a drive surface 34. The drive surface 34 is adapted to permit the engagement of drive means 35, thereby permitting synchronized mechanical communication between the cantilevered arms or cam levers 28. It will be appreciated that drive means 35 may be unsynchronized.

In a preferred embodiment, the drive means 35 may comprise a belt engaging a pully surface 34. In an alternative embodiment, the drive means 35 may comprise a chain engaging teeth or sprockets 34. In yet another embodiment, the drive means 35 may comprise a gearing arrangement. It will be appreciated that hydraulic means may also be used to actuate the cantilevered arms 28.

Figure 2:
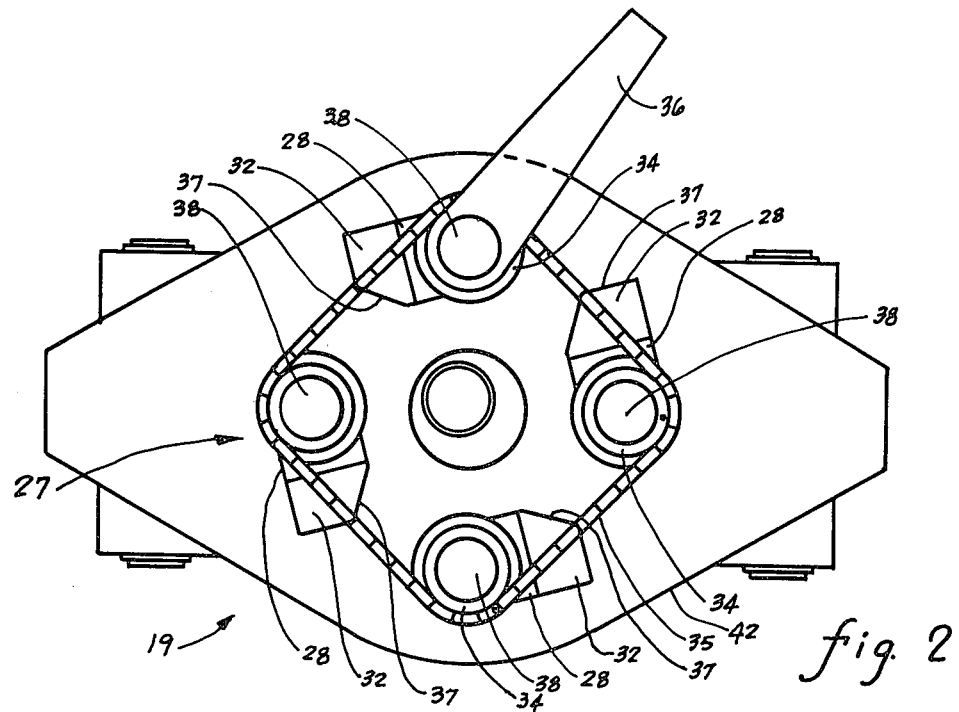
FIG. 2 shows an end view of the pipe capping apparatus of FIG. 1 illustrating the centralizer.

Referring to FIG. 2, the centralizer is shown in an open position. Actuation means 36 is shown connected to a first cam arm pivot point 38. The cantilevered arms 28 are mechanically coupled to the handle 36 through the drive means 35 engaging the drive surface 34 of the cam levers or arms 28.

In FIG. 2, the pipe 26 is shown in an off-center position.

The interchangeable cam pieces 32 have a cam surface 37. Alternatively, the cantilevered arms or cam levers 28 may be formed into one piece without the interchangeable cam pieces 32.

Figure 3:
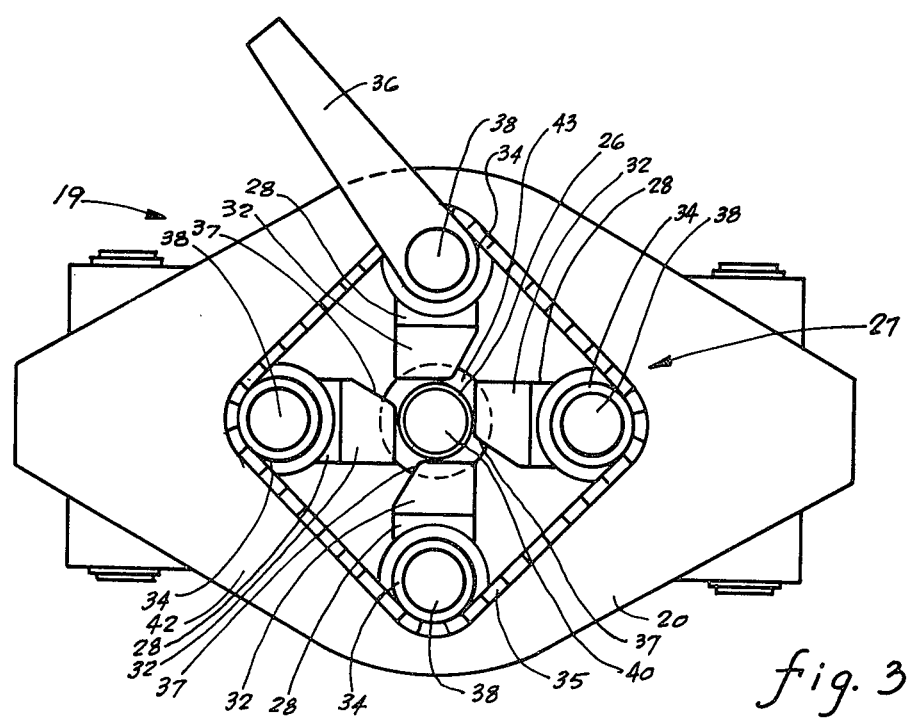
FIG. 3 shows another end view of the centralizer.

As shown in FIG. 3, when the handle 36 is rotated about the first cam lever pivot point 38, the cam levers or cantilevered arms 28 are rotated by the drive means 35. Rotation of the cantilevered arms 28 causes the pipe 26 to contact one or more of the cam surfaces 37. The cam surfaces 37 are adapted to urge or cam the pipe 26 into an axially centered position. Thus, the centralizer 27 is adapted to axially center the pipe 26 using a single motion or movement.

It will be appreciated that the cantilevered arms 28 may be independently operated in order to center the pipe 26. In a preferred embodiment, the cantilevered arms 28 operate simultaneously and are equiangularly disposed about the pipe receiving zone 43 of the body 20.

The jaw assembly 21, illustrated in FIG. 1, comprises a jaw holder 45, a fastening means 46, a jaw tooth segment 47, and an alignment key 48. Fastening means 46 may be a bolt, screw, pin or other mechanism adapted to fasten the jaw holder 45 to the jaw tooth segment 47.

The jaw holder 45 has a load recess 49. The jaw tooth segment 47 has a load protuberance 50. The load recess 49 is adapted to receive the load protuberance 50. During pressurization of the pipe 26, a shear force develops against the load protuberancce 50 which is inserted within the load recess 49. The load protuberance 50 is adapted to withstand the shear force exerted upon it by the jaw holder 45 at a load interface 131. The load protuberance 50 may comprise steel lugs, and in practice heat heated steel lugs have provided satisfactory results. The load protuberance 50 and the jaw holder 49 permit the jaw tooth segment 47 to be held securely by the jaw holder 45 and inhibit the jaw tooth segment 47 from sliding axially against the jaw holder 45.

The jaw holder 45 has a jaw segment receiving face 52. A first key way slot 53 is located on the jaw segment receiving face 52. The jaw tooth segment 47 has a face adapted to abut against the jaw segment-receiving face 52 of the jaw holder 45. The jaw tooth segment 47 has a second key way slot 51. The second key way slot 51 is adapted to align with the first key way slot 53 such that when a alignment key 48 is inserted therein the jaw tooth segment 47 is properly aligned with the jaw holder 45.

In a preferred embodiment, the contiguous faces of the jaw holder 45 and the jaw tooth segment 47 are congruent. It will be appreciated that the jaw 21 may alternatively be constructed as a one piece embodiment.

In the illustrated embodiment having two arms 22 and 57 shown in FIG 1, the first arm 22 has a first spring-fastening extension or spring anchor 54 joined to it near the second pivot point 24. This spring-fastening extension 54 has connected to it one end of an elastic member, resilient member or spring 55.

The spring 55 has its other end connected to a second spring-fastening extension or spring anchor 56. The first spring-fastening extension 54 and the second spring-fastening extension 56 are offset from the axis A of the body 20 in order that the elastic member 55 may be extended therebetween without interfering with the axial placement of the pipe 26. The second spring-fastening extension 56 is joined or connected to a second arm 57. The second arm 57 is connected to a second jaw or jaw assembly 58 at a fourth pivot point 59. The second arm 57 is connected to the body 20 at a third pivot point 60. Thus, a second radial force translator 61 comprises the second arm 57, the third pivot point 60, the fourth pivot point 59 and the second jaw 58. The operation of the second arm 57, the third pivot point 60, the fourth pivot point 59 and the second jaw 58 is similar to the operation of the first arm 22, the first pivot point 23, the second pivot point 24 and the first jaw 21, respectively.

The elastic member 55 is adapted to urge the first arm 22 and the second arm 57 radially inwardly. When the pipe 26 is actually inserted into the body 20, the elastic member 55 urges the first jaw 21 and the second jaw 58 into engagement with the pipe 26. In a preferred embodiment, the elastic member 55 is adapted to urge the jaws 21 and 58 to exert a pressure of substantially 15 psi upon the outer surface of the pipe 26. The elastic member 55 is used to initially urge the jaws 21 and 58 into contact with the pipe 26. Once engaged, the force upon the jaws 21 and 58 will increase in proportion to the pressure asserted upon the interior zone 41 of the body 20, which is translated to the jaws 21 and 58 throgh the first radial translator 39 and the second radial translator 61, respectively.

It will be appreciated that the elastic member 55 may be replaced by equivalent means adapted to urge the jaws radially inwardly. For example, a spring may be placed between the first arm 22 and the inner surface of the body 20, which is compressed when the first jaw 21 is urged radially outardly, thus providing a counterforce urging the first jaw 21 radially inwardly. A similar spring could be provided for each jaw or arm.

Many pipes that require testing have threads and couplings upn their ends. Many prior art devices can damage pipe threads during use. To facilitate the insertion and removal of the pipe 26, a first bumper 62, a second bumper 63 and a third bumper 64 are provided in a preferred embodiment of my invention, as shown in FIG. 1. In a preferred embodiment, the first bumper 62, the second bumper 63 and the third bumper 64 are elastomer members or bumpers. The first bumper 62 protects the pipe threads upon initial insertion of the pipe 26 into the centralizer 27 and the pipe receiving zone 43 of the body 20.

The second bumper 63 protects the threads of the pipe 26 upon insertion of the end of the pipe 26 into the interior zone 41 of the body 20. The third bumper 64 is adapted to permit the initial abutment of the end of the pipe 26 against the inner surface of the body 20. During hydrostatic pressure testing, the pipe 26 will be urged away from the elastomer bumper 64 by the fluid pressure upon the interior 40 of the pipe 26 and the interior zone 41 of the body 20. However, actual tests have shown that little or no actual movement is observable. To facilitate fluid communication between the interior zone 41 of the body 20 and the passageway 72, a notch 64 is provided in the bumper 73.

It is desirable to have a hydrostatic testing apparatus capable of testing pipe of varying diameters. Moreover, it is desirable to have a hydrostatic testing apparatus adapted to receive upset tubing or couplings.

An adaptor 66 and a threaded seal nut 65 are removably engagable within the front portion of the body 20, as shown in FIG. 1. The adaptor 66 and the seal nut 65 contain are used to provide a pressure tight seal for several different pipe sizes as desired. It will be appreciated that when only one size of plain end pipe 26, is to be tested, the adapter 66 is unnecessary and the seal nut 65 is screwed directly into the body 20.

In a preferred embodiment, the adaptor 66 is threadably engaged within the rear portion of the body 20. Thus, the adaptor 66 may be screwed into the body 20 to permit the adaptor 66 to be inserted or removed when required. The seal nut 65 is threadably engaged or screwed into the adaptor 66. The second elastomer bumper 63 is molded upon or adhesively affixed to the seal nut 65.

During hydrostatic testing of the pipe 26, it is desirable to introduce fluid, usually water, into the interior 40 of the pipe 26 and into the interior zone 41 of the body 20. Referring to FIG. 1, an axial passage, tube, opening or aperture 67 is shown generally axially centered within the rear of the body 20. In a preferred embodiment, threads are provided upon the interior of the axial passage 67 to permit the attachment of a pipe or a tube 68 to the body 20.

The axial passage 67 is in fluid communication with the interior zone 41 of the body 20 and the interior 40 of the pipe 26.

During the hydrostatic testing of the pipe 26 at high pressure levels, it is important to remove all air or other gas from the interior 40 of the pipe 26, and from the interior zone 41 of the body 20. Failure to remove all of the air may create a hazard of explosion. High pressure hydrostatic testing may be hazardous and unsafe unless substantially all of the air or gas is removed from the interior 40 of the pipe 26.

Referring to FIG. 1, the hydrostatic testing apparatus includes a feature comprising an air purge valve 69. The purge valve 69 comprises a control port 70 joined or secured to a stem 71. A passageway 72 joins the purge valve 69 to the interior zone 41 of the body 20. The passageway 72 is adapted to place the purge valve 69 in fluid communication with the interior zone 41. In a preferred embodiment, the purge valve 69 is vertically connected to the body 20. The stem 71 is placed in fluid communication with the highest point of the interior zone 41 of the body 20. Thus, as air bubbles normally accummulate at the highest portion of the interior zone 41 of the body 20, these air bubbles may be removed by opening the control port 70.

In a preferred embodiment, fluid is introduced into the axial passageway 67 from a fluid source having check valves of a conventional type, thus filling the interior zone 41 of the body 20 and the interior 40 of the pipe 26. It will be appreciated that filling may be effected from the opposite end of the pipe 26. During filling, the purge valve 69 is opened by means of the control port 70. Air present in the interior zone 41 of the body 20 wil be urged upward by the fluid introduced into the interior zone 41, and the air within the pipe would thus be urged up through the stem 71 and out the control port 70. The mixture of fluid and air exiting through an orifice in the control port 70 will normally be visually observable as a sputtering mixture of fluid and gas. When the sputtering stops and a solid stream of fluid or water begins to emerge from the purge valve 69, the purge valve 69 may be closed by means of the control port 70. Thus, the purge valve 69 is adapted to safely expunge substantially all the air or gas within the region 41 of the body 20 and the interior 40 of the pipe 26.

The pipe 26 will preferably not be in fluid-tight engagement with the third bumper 64. In a preferred embodiment, a notch, slot or second passageway 73 is provided in the third bumper 64 to facilitate fluid communication between the interior zone 41 of the body 20 and the passageway 72.

It is desirable during pressurization to provide a seal-tight engagement between the body 20 and the pipe 26. When the adaptor 66 and the seal nut 65 are inserted within the body 20, it is desirable to provide a fluid-tight seal or a pressure barrier between the pipe 26 and the adaptor 66.

Referring to FIG. 1, a first pressure barrier apparatus 75 and a second pressure barrier apparatus 74 are shown.

The first pressure barrier apparatus 75 may be a flexible member or seal. The second pressure barrier apparatus 74 is similarly constructed.

The seal nut 65 is adapted to hold the first seal 75 in place as shown in FIG. 1. The seal nut 65 permits the seal 75 to be easily replaced, if desired. If the adapter 66 is not used, only one seal 74 will be required.

The pressure barrier apparatus 75 and 74 is depicted in greater detail in FIG. 7. As may be seen in FIG. 7, the pressure barrier apparatus 75 comprises a first lip 76 and a second lip 77 connected to a body 78. The pressure barrier apparatus 75 is a flexible member and is adapted to permit the flexible movement of the first lip 76 and the second lip 77. The first lip 76 and the second lip 77 are adapted to spreadably engaged a first surface 89 of the body 20 and a second surface 90 of the pipe 26, respectively, thereby defining an inner zone 83 and an outer zone 82 (see FIG. 8) when the first and second lips 76 and 77 are urged respectively against the first and second surfaces 89 and 90 during pressurization.

The operation of the seals 74 and 75 when an adapter 66 is employed is equivalent. A first lip 76 of the pressure barrier apparatus 74 contacts a first surface of the body 20 and a second lip 77 contacts a second surface of the adapter 66. Similarly, a first and second lip 76 and 77 of the first apparatus 75 contact a first and second surface of the adapter 66 and the pipe 26, respectively.

Referring to FIG. 7, the first lip 76 and the second lip 77 define a pressure zone 79. During pressurization, fluid is introduced into the fluid pressure zone 79, thus urging the first lip 76 and the second lip 77 apart. The first lip 76 is adapted to displace or dispose toward the inner surface of the body 20. The second lip 77 is adapted to displace toward the outer surface of the pipe 26.

A front view of the flexible member 75 is shown in FIG. 6. A plurality of lugs 80 are shown formed upon the second lip 77. The lugs 80 define interstices 81. The interstices 81 are in fluid communications with the pressure zone 79. The interstices 81 are also in fluid communication with the passageway 72.

It will be appreciated that the lugs 80 may also be formed upon the first lip 76.

As depicted in FIG. 8, the flexible member 75 is adapted so that the first lip 76 disposes against the inner surface of the body 20. The second lug 77 is adapted to displace toward the outer surface of the pipe 26. The flexible member thus defines an inner zone 83 and an outer zone 82. The inner zone 83 is filled with fluid during pressurization. The flexible member 75 thus forms a pressure barrier between the inner zone 83 and the outer zone 82.

Preferably, the second lip 77 is relatively long in order to provide a large area of engagement with the surface of the pipe 26 to facilitate a fluid-tight seal where the surface of the pipe 26 is rough, rusty or dirty.

It is desirable to pre-stress the second lip 77 so that the second lip 77 is urged into engagement with the outer surface of the pipe 26. This is accomplished by the lug 80. The lug 80 has a length measured radially sufficient to urge the second lip 77 into engagement with the outer surface of the pipe 26. Thus, when little or no pressure is applied to the inner zone 83, the lug 80 urges the second lip 77 into sealing engagement with the outer surface of the pipe 26 and inhibits leakage of fluid into the outer zone 82.

The interstices 81 place the pressure zone 79 into fluid communication with the inner zone 83. The inner zone 83 is in fluid communication with the passageway 72. Introduction of fluid into the interior zone 41 of the body 20 (shown in FIG. 1) permits fluid to enter the passageway 72 and the inner zone 83 illustrated in FIG. 8. The interstices 81 permit fluid to enter the pressure zone 79. Pressurization of the fluid thus urges the second lip 77 into engagement with the outer surface of the pipe 26.

Flushing of the pressure zone 79 is desirable to effect the removal of dirt, rust, debris and other matter that may accummulate within the pressure zone 79. Thus the lugs 80 facilitate the flow of liquid through the pressure zone 79 and thereby permit the pressure zone 79 to be flushed by the fluid. The pressurization and depressurization of the fluid thus flushes out the pressure zone 79 and tends to remove dirt, debris and other foreign matter that may otherwise accummulate within the pressure zone 79.

It is also desirable to remove substantially all air trapped within the pressure zone 79 of the flexible member 75 to reduce the hazard of explosion. The lugs 80 also 75 to reduce the hazard of explosion. The lugs 80 also facilitate the removal of air from the pressure zone 79. Referring to FIG. 1, the purge valve 69 is placed into fluid communication with the pressure zone 79 defined by the flexible member 74. In a preferred embodiment, the stem 71 of the purge valve 69 is positioned adjacent the pressure zone 79 at the highest point of the pressure zone 79 within the body 20. Thus, the purge valve 69 also facilitates the removal of air or other gas from the pressure zone 79. This further reduces the hazard of explosion that could result if air remained within the hydrostatic testing apparatus 19.

FIG. 1 shows a cross sectional view of the seal or pressure barrier apparatus 74 or 75. It is contemplated that the seals 74 and 75 will be formed into circular rings. However, the seals 74 and 75 may be any shape depending upon the shape of the contiguous surfaces of the body 20, the pipe 26, and the adapters 66 and 65.

Referring to FIG. 9, an alternative embodiment of the pressure barrier apparatus is shown which is suitable for relatively high pressure hydrostatic testing. The pressure barrier apparatus 75 comprises a flexible member 88 having a first lip 76 and a second lip 77 joined to a body, and a spacer 84 and a sealing ring 85. The flexible member 88 is constructed similarly to the flexible member described with reference to the embodiment of the pressure barrier apparatus 75 depicted in FIG. 6, FIG. 7 and FIG. 8.

The first lip 76 is disposed against a first surface 89 of the body 20. The second lip 77 is adapted to engage a second surface 90 of the pipe 26. The lug 80 urges the second lip 77 radially inwardly toward the second surface 90, and also forms interstices, as shown in FIG. 6, permitting fluid communication between the pressure zone 79 and the inner zone 83.

Referring to FIG. 9 the spacer 84 is located radially rearwardly of the flexible member 88. The sealing ring 85 is located radially rearwardly of the spacer 84. Thus, the spacer 84 is interposed between the flexible member 88 and the ring 85. The spacer 84 permits the flexible member 88 and the ring 85 to reciprocally slide against each other in a generally radial direction.

The ring 85 is preferably made of metal. The ring 85 may be made of steel, as in a preferred embodiment; but it is also contemplated that the ring 85 may be fashioned from beryllium copper or aluminum.

The ring 85 rests against a sloped or cam surface 87 of the body 20. If an adapter 66 is utilized, the cam surface 87 will be in the adapter 66. The body 20 also has an indentation or groove forming a spacer stop gap 86, best shown in FIG. 9A. When little or no pressure is applied to the inner zone 83, the ring 85 will normally rest generally in the position shown in FIG. 9.

During hydrostatic testing, pressurized fluid is introduced into the passageway 72, the inner zone 83, and the pressure zone 79, as shown in FIG. 10. Relatively high pressures could cause the flexible member 88 to extrude into the space between the body 20 and the pipe 26, generally shown in FIG. 9 as outer zone 82.

As best shown in FIG. 10, during pressurization the flexible member 88 is urged generally axially rearwardly. The flexible member 88 urges the spacer 84 axially rearwardly. The spacer 84 thus urges the ring 85 axially rearwardly and causes the ring 85 to slide rearwardly along the sloped or cammed surface 87 of the body 20. The sloped surface 87 causes the ring 85 to contract radially inwardly and tend toward the outer surface 90 of the pipe 26.

If the pressure is sufficiently high and if the size of the pipe 26 permits, the spacer 84 will slide radially rearwardly until it occupies the spacer stop gap 86 in the position shown in FIG. 10A. The flexible member 88 and the spacer 84 move axially rearwardly. The flexible member 88 and the spacer 84 urge the ring 85 axially rearwardly and radially inwardly as it slides along surface 87 of the body 20. Preferably, the ring 85 should be urged into contact with the surface 90 of the pipe 26. As shown in FIG. 10, the ring 85 inhibits the extrusion of the flexible member 88 during relatively high pressure testing.

As shown in FIG. 10B, some extrusion of the flexible member 88 may occur within the zone between the spacer 84 and the pipe 26. This amount of extrusion is normally acceptable.

FIG. 11 shows a front cross sectional view of the ring 85 taken along section line 11—11 in FIG. 9. The ring 85 may be a resilient ring having an expansion gap 91 between the ends thereof. FIG. 11 corresponds to the unpressurized or low pressure position of the ring 85 shown in FIG. 9.

FIG. 12 shows the ring 85 during high pressure testing in a position that corresponds to the relative position of the ring 85 shown in FIG. 10 during pressurization. Preferably, the ends of the ring 85 may come into contact during pressurization.

FIG. 13 shows an alternative embodiment of the ring 85 having slanted ends forming an expansion gap 91. As shown in FIG. 14, the ends of the ring 85 may come into contact during relatively high pressurization.

It will be appreciated that the effective diameter of the ring 85 is larger when the ring 85 is in the position shown in FIG. 9, as compared to the diameter of the ring 85 when it is in the position shown in FIG. 10. The embodiments of the ring illustrated in FIGS. 11 through 14 illustrate how the ring 85 is permitted to expand to the position shown in FIG. 9. It will be appreciated that the embodiment disclosed in FIGS. 13 and 14 permits contraction of the diameter of the ring 85 even after the ends of the ring 85 have come into contact in the position shown in FIG. 14. The slanted ends of the ring 85 may continue to slide against each other and permit continued contraction of the diameter of the ring 85 if necessary.

The pressure barrier apparatus 75 and in FIGS. 6, 7 and 8, and the flexible member 88 shown in FIGS. 9 and 10, may be constructed similarly. The flexible member 88 may be formed from polyurethane, commonly referred to as urethane. Fine powered molybdenum disulfide is cast with the polyurethane during the fabrication process. The molybdenum disulfied facilitates lubricity between the flexible member 88 and the pipes 26 which are normally repeatedly inserted into and removed from the body 20 during testing. Preferably, the flexible member 88 comprises a polyurethane ester base material, but it is contemplated that an ether base polyurethane may also be used. An ester base material has good properties with respect to an environment involving a substantial exposure to water.

In a preferred embodiment, the flexible member 88 comprises a polyurethane, ester base, 85 durometer (shore A) seal cast with fine powered molybdenum disulfide. The flexible member 88 may be diamine cured.

As best shown in FIG. 7, the lips 76 and 77 should be relatively long as compared to the length, measured axially, of the member body 78. In a preferred embodiment, the second lip 77 is substantially twice as long as the length measured axially of the member body 78. Preferably, the first lip 76 may be longer than the second lip 77, facilitating fluid communication between the inner zone 83 and the passageway 72. The first lip 77 length may be preferably determined by multiplying the thickness, measured radially, of the member body 78 by a factor of two or more. Preferably, the second lip 77 should be substantially thicker than the first lip 76. In practice, a second lip 77 substantially twice as thick as the first lip 76 has provided satisfactory results. This construction is adapted to enhance the relative abrasion resistivity of the second lip 77 to increase its ability to withstand wear, thus reducing the incidence of replacement of the seal 75.

Preferably, the flexible member 88 should be fabricated from a material having a high compressive strength that is tear resistant and abrasive resistant. Alternative materials that may be used include rubber or elastomer, in addition to polyurethane.

Illustrated in FIGS. 4 and 5 is an alternative embodiment of the jaw 21.

Referring to FIG. 5, the jaw 21 is connected to an arm 22 at a second pivot point 24. The arm 22 comprises a first link 93 and a second link 94, as shown in FIG. 4. It has been found that links 93 and 94 provide a superior embodiment for the arm 22. The dual links 93 and 94 yield an arm 22 having superior structural features over a single link arm. The dual links 93 and 94, among other things, permit the jaw 21 to be pivotally connected to the body 20 in a more stable configuration. Actual tests have proven the superior stability of the dual links 93 and 94 embodiment of the arm 22. The dual links 93 and 94 also permit the construction of a practical hydrostatic testing apparatus 19 having only two jaws 21.

Referring to FIG. 5, the jaw 21 comprises a jaw holder 95 and a jaw tooth segment 96, pivotally connected with a pin 97.

The jaw tooth segment 96 has a friction surface 92 shown in FIG. 4 which is adapted for gripping the pipe 26. In a preferred embodiment using two jaws 21 for gripping the pipe 26, the friction surface 92 of the jaw tooth segment 96 is adapted to grip substantially half of the circumference of the pipe 26. Preferably, the distance "X" shown in FIG. 4 is substantially ½ inch. Thus, it will be appreciated that approximately all but one inch of the pipe 26 circumference is gripped by the two jaws 21.

The jaw holder 95 has a load recess 98. The jaw tooth segment 96 has a corresponding load protuberance or load lug 99. During pressurization, the jaw tooth segment 96 will be urged generally axially rearwardly. Thus, a generally axial shear force will be borne by the load protuberance 99 at the load interface 100.

As shown in FIG. 5, the load protuberance 99 is in a generally axially forward position with respect to the jaw holder 95. This enhances the shear force bearing properties of the jaw holder 95. It will be appreciated that the load protuberance 99 may comprise one or more lugs fashioned from steel, or some other material having an ultimate yield sufficient to withstand the shear force that will be developed across the load interface 100 as a result of pressurization. The required ultimate yield of the material will depend upon the maximum test pressure that will be applied to the pipe 26.

Because the load protuberance 99 and the load interface 100 located in the load recess 98 bears the load, the pin 97 does not bear a significant portion of the load. As shown in FIG. 4, the jaw holder 95 has a first boss ledge 101 and a second boss ledge 102. The jaw holder 95 has a corresponding first channel 103 and a second channel 104. The first channel 103 is adapted to receive the first boss ledge 101. Similarly, the second channel 104 is adapted to receive the second boss ledge 102. As shown in FIG. 4, the radially inward force exerted by the jaw holder 95 upon the jaw tooth segment 96 is substantially borne at the interfacing surfaces between the first and second channels 103 and 104 and the first and second boss ledges 101 and 102, respectively.

The pin 97 is inserted axially into a pin-receiving aperture 105 in the jaw holder 95.

It is desirable to permit movement of the jaw tooth segment 96 radially to facilitate the engagement of the first and second channel 103 and 104 with the first and second boss ledges 101 and 102. Thus, as shown in FIG. 4, the pin receiving aperture 105, in a preferred embodiment, has a generally eliptical cross sectional area. The pin receiving aperture 105 forms a slot which permits the pin 97 to move radially outward until the first and second channels 103 and 104 engage the first and second boss ledges 101 and 102.

The jaw tooth segment 96 has a pin-receiving aperture or channel 106 extending through the upper portion of the jaw tooth segment 96 generally parallel to the axis of the body 20 or the pipe 26. The pin receiving aperture 106 has a generally circular cross sectional area, in a preferred embodiment. The pin receiving aperture 106 may be any shape which conforms to the shape of the pin 97.

As shown in FIG. 5, the pin 97 seats in the pin receiving aperture 106. It will be appreciated that movement of the pin 97 within the pin receiving slot 105 permits the jaw tooth segment 96 to move generally radially with respect to the pipe 26, thus permitting the first and second boss ledges 101 and 102 to seat within the first and second channels 103 and 104. The pin 97 is held in place by keepers, or washers 107.

It is desirable to evenly distribute the generally radially inward force exerted upon the jaw tooth segment 96 by the jaw holder 95 evenly across the outer surface of the pipe 26. The generally parallel alignment of the pin 97, the pin receiving aperture 106, and the pin receiving slot 105 permits the jaw tooth segment 96 to evenly engage the pipe 26. As shown in FIG. 4, the jaw tooth segment 96 is adapted to evenly distribute the radially inward gripping force across the outer surface of the pipe 26.

It will be appreciated that the embodiment of the jaw assembly 21 illustrated in FIGS. 4 and 5 does not require a pin 97 of sufficient strength to withstand the forces described above. This embodiment does not require large shear forces to be withstood by the pin 97 and is therefore more advantageous in this respect.

Referring to FIG. 1, it will be appreciated that the jaw assembly 21 may be a single piece, as is illustrated in the embodiment shown in FIG. 4 and FIG. 5, or in FIG. 15.

It will be appreciated that the second pivot point shown in FIG. 4 and FIG. 5 may comprise a pin 24 held in place by keepers 108. Referring to FIG. 1, the first, second, third and fourth pivot points 23, 24, 60, and 59 may be similarly constructed.

FIG. 15 illustrates and alternative embodiment of the jaw assembly 21. In the illustrated embodiment, the jaw assembly 21 comprises a single piece jaw 21 having a friction surface 92. Dual links 93 and 94 connect the jaw 21 to the body 20. The jaw 21 is pivotally connected to the dual links 93 and 94 at a second pivot point 24. The dual links 93 and 94 are substantially parallel to each other in a plane transversing the axis A of the body 20.

In a preferred embodiment, the friction surface 92 shown in FIGS. 1, 4 and 15 may comprise teeth or serrations for the purpose of increasing the coefficient of friction of the friction surface 92. It has been found that teeth may be required if the surface of the pipe 26 is dirty. The translation angle T may be adjusted to reduce the radial gripping force exerted by the jaw assembly 21 upon the pipe 26 if necessary to avoid damage to the pipe 26 by the teeth 92. If the pipe 26 is smooth, then the friction surface 92 may comprises grooves or fine serrations. It will be appreciated by those skilled in the art that other surfaces may be employed as a friction surface 92 with some degree of utility.

Figure 16:
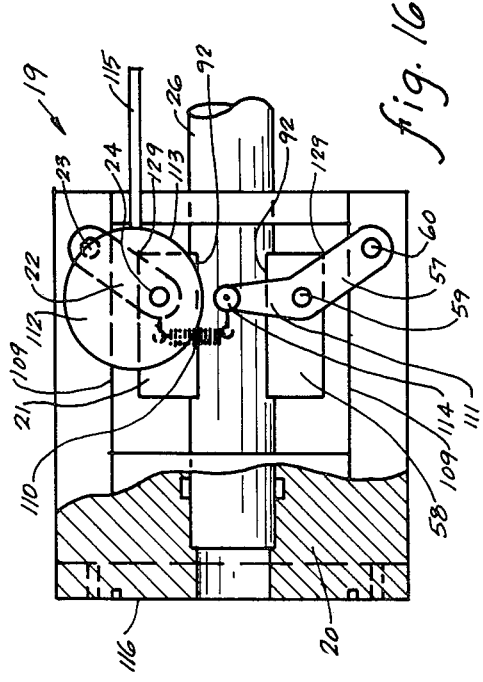
FIG. 16 is a partial cross-sectional side view of an alternative embodiment of the means for engaging and disengaging the jaws upon the pipe.

FIG. 16 illustrates an alternative embodiment of a hydrostatic testing apparatus 19 illustrating an alternative means for grasping the pipe 26. It will be appreciated that the means for grasping the pipe 26 illustrated in FIG. 16 may be employed with utility in other applications where it is desirable to grasp a round or tubular cylinder. The grasping means comprises a first arm or link 22 pivotally connected to the body 20 at a first pivot point 23. The first arm 22 is pivotally connected to a first jaw 21 at a second pivot point 24. A second arm 57 is pivotally connected to a generally opposite side of the body 20 at a third pivot point 60. The second arm 57 is pivotally connected to a second jaw 58 at a fourth pivot point 59.

A wheel or cam 112 is eccentrically rotatably connected to the second pivot point 24. The wheel 112 has an outer bearing surface 113.

The second arm 57 has an extension, projection, finger or leg 111 extending from the radially inward end of the second arm 57 near the second pivot point 59. In a preferred embodiment, the extension 111 projects from the second arm 57 at an angle generally perpendicular to the axis of the body 20 when the jaws 21 and 58 are engaged against the surface of the pipe 26.

The extension 111 has a cam roller 114 attached to the tip of the extension 111 as shown in FIG. 16. The roller 114 is rotatably mounted to the end of the extension 111.

An elastic member or spring 110 is connected to the end of the extension 111 and to the first arm 22. It will be appreciated that the spring 110 may be connected in any manner which will tend to urge the first arm 22 and the second arm 57 axially inwardly. The elastic member 110 tends to urge the first and second jaws 21 and 58 into initial engagement with the tubular cylinder 26.

Figure 17:
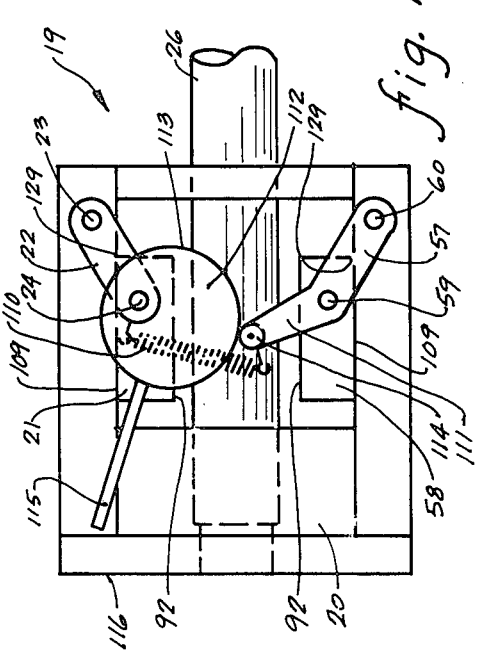
FIG. 17 is an additional side view of the embodiment disclosed in FIG. 16 showing the jaws retracted.

Referring to FIG. 17, when the wheel 112 is rotated in a first sense, which is in a counterclockwise direction in the embodiment illustrated in FIGS. 16 and 17, the bearing surface 113 of the wheel 112 contacts the roller 114 of the extension 111 and urges the first and second jaws 21 and 58 radially outwardly. If only one of the jaws 21 and 58 disengages the pipe 26, the jaw disengaged 21 or 58 will be caused to contact the inner surface 109 of the body 20 by rotation of the wheel 112. Further rotation of the wheel 112 will then urge the other jaw 21 or 58 to disengage the pipe 26.

The elastic member 110 is adapted to urge the first and second arms 22 and 57 radially inwardly and thus urge the wheel 112 in a rotational sense opposite the first sense, or clockwise in FIGS. 16 and 17.

Actuation means 115 is provided to initiate the rotation of the wheel 112. In a preferred embodiment, actuation means 115 may comprise a handle 115 as shown in FIGS. 16 and 17. It will be appreciated that rotation of the wheel 112 may be actuated by conventional means.

FIG. 16 also illustrates an embodiment of the body 20 showing a flange 116 fashioned upon a front face of the body 20. The flang 116 can be made integrally with the body 20 to permit a weldless flanged connection to be made to a plain end pipe. With the illustrated embodiment, two testing apparatus 19 may be placed front to front for adjoining to plain end pipes where welding is not available as, for example, in a hazardous area.

Figure 18:
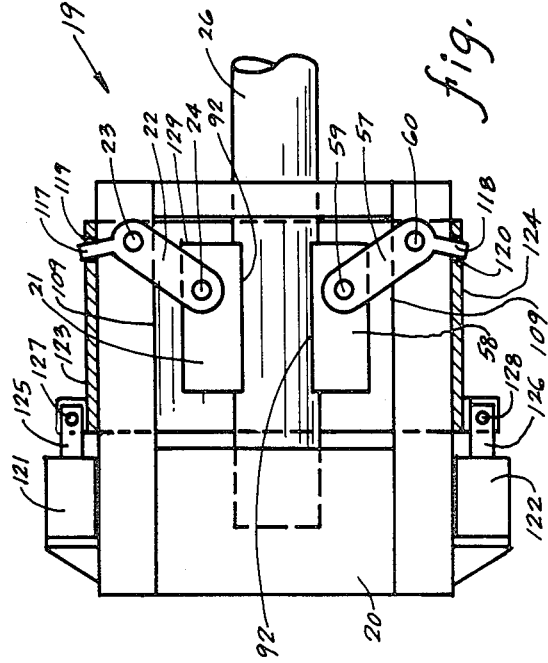
FIG. 18 depicts a side view of another alternative embodiment of the means for engaging and disengaging the jaws upon the pipe.
Figure 19:
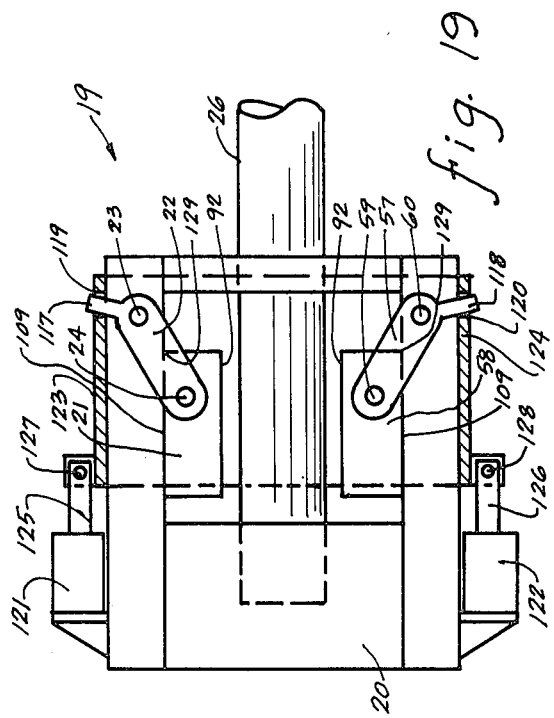
FIG. 19 shows an additional side view of the apparatus illustrated in FIG. 18 showing the jaws retracted.

Illustrated in FIG. 18 and FIG. 19 is an alternative embodiment of a means for engaging and disengaging the jaws 21 and 58 upon the outer surface of the pipe 26. A first arm 22 is pivotally connected to the body 20 at a first pivot point 23. A second arm 57 is pivotally connected to a generally opposite side of the body 20 at a third pivot point 60. The first and second arms 22 and 57 are pivotally connected to a first and second jaw 21 and 58 at a second and fourth pivot point 24 and 59, respectively, in a manner similar to that described with reference to the embodiment illustrated in FIGS. 16 and 17.

The first arm 22 has an extension, offshoot or appendage 117. The second arm 57 has a similar second extension 118. The first and second extensions 119 and 118 are connected to the first and second arms 22 and 57 near the end of the arms 22 and 57 attached to the body 20.

The first extension 117 is connected to a first guide sleeve or such sleeve 123 at a shoe or fastening means 119. The second extension 118 is similarly connected to a second guide sleeve or synch sleeve 124 at a second shoe or fastening means 120. A first and second actuation means 121 and 122 are connected to the body 20. First actuation means 121 has a first shaft 125 connected to the first guide sleeve 123 by fastening means 127. The second actuation means 122 has a second shaft 126 connected to the second guide sleeve 124 by a second fastening means 128.

It will be appreciated that the first and second jaws 21 and 58 have friction surfaces 92 adapted to grip the pipe 26.

The actuation means 121 and 122 may be fluid cylinders which are hydraulically operated; or alternatively manually operated screws, levers and other conventional mechanisms may be utilized.

As best shown in FIG. 19, the actuating means 121 urges the first guide sleeve or synch sleeve 123 generally rearwardly along the body 20. The first guide sleeve 123 is adapted to reciprocally slide against the body 20. As the first sleeve 123 slides against the body 20, it rotates the first arm 22 about the first pivot point 23, thus disengaging the first jaw 21 from the pipe 26. The inner surface 109 of the body 20 contacts the jaw 21 and is adapted to afford the complete disengagement of the friction surface 92 from the pipe 26. If the rear end of the first jaw 21 disengages the pipe 26 first, the axially remote rear upper corner 129 of the first jaw 21 will contact the inner surface 109 of the body 20. Further rotation of the first arm 22 will tend to cause the first jaw 21 to pivot about the point where the corner 129 contacts the surface 109. Thus, further rotation of the first arm 22 will facilitate the disengagement of the front end of the first jaw 21 from the pipe 26. It will be appreciated that the jaws 21 and 58 shown in FIG. 1 may also contact the inner surface of the body 20 during disengagement in the same manner as that described above.

The second actuation means 122, second guide sleeve 124, second arm 57 and second jaw 58 operate in a similar manner.

The means for engaging and disengaging the jaws 21 and 58 from the pipe 26 illustrated in FIGS. 18 and 19 has utility in applications where accurate alignment of the jaws 21 and 58 is desirable. The sleeves 123 and 124 are well adapted to permit precise alignment of the jaws 21 and 58, respectively, by adjusting the position of the extensions 117 and 118 upon the sleeves 123 and 124, respectively. It will be appreciated that conventional adjustment means may be provided for adjusting the position of the extensions 117 and 118 upon the sleeves 123 and 124. It will also be appreciated that the sleeves 123 and 124 may be formed into a single sleeve substantially encircling the body 20.

It will be appreciated by those skilled in the art that the jaws 21 and 58 may be fixedly connected to the arms 22 and 57. Such an embodiment would preferably include a counter-sunk zone within the inner surface 109 of the body 20 to permit the radially outward rotation of the jaws 21 and 58.

SUMMARY AND ADVANTAGES OF THE INVENTION

It will be appreciated that in constructing a cylinder gripping apparatus according to the present invention, certain significant advantages are provided.

In particular, a cylinder gripping apparatus according to the present invention permits a cylinder, pipe or tube to be held by a gripping force which is proportional to an axial force tending to urge the cylinder, pipe or tube in an unwanted direction. A cylinder gripping apparatus according to the present invention provides an interfacing assembly which develops a radial counterforce or gripping force in response to an axial force upon the cylinder which is proportional to the axial force. Thus, as the axial force tending to urge the cylinder in an unwanted direction increases, the gripping force will increase proportionally in response to the increase axial force.

In addition, a cylinder gripping apparatus according to the present invention provides an interfacing assembly which is more economically constructed and which is adapted to withstand greater forces between the jaw and the body. The elimination of arms which are pivotally connected by pins to the jaw and the body eliminates the requirement that the pins be sufficiently strong to withstand the forces between the arm and the body.

Moreover, the cylinder, pipe or tube need not be perfectly centered within the body. A cylinder gripping apparatus according to the present invention permits the jaw to move transversely with respect to the axis of the body and thereby align into engagement with a cylinder which is deformed or which is not perfectly centered within the body.

A cylinder gripping apparatus according to the present invention includes the further advantage of providing an interfacing assembly which may be used in connection with a hydrostatic testing apparatus for high pressure testing. The interfacing assembly is adapted to withstand greater forces than the embodiment disclosed in the prior art.

A cylinder gripping apparatus according to the present invention includes the further advantage of providing utility as a snubber, safety hanging apparatus or blowout preventer for use in connection with wellhead operations. In such an application, the cylinder gripping apparatus provides the advantage of jaws which do not have to be completely released from the pipe in order to pass couplings. Thus, the risk of dropping the pipe or having a blowout while couplings are being passed is avoided. A blowout preventer, snubber or safety hanging apparatus constructed according to the present invention will provide a safety feature in that the gripping force generated will be proportional to the axial and Torsional forces upon the pipe.

A cylinder gripping apparatus according to the present invention may employ offset floating lugs which provide the advantage of a gripping force which is also proportional to the rotational forces or torque upon the cylinder, tube of pipe being gripped. The offset floating lugs act as tongs to prevent rotation, in addition to gripping the pipe to prevent axial movement.

A platform jacking apparatus constructed in accordance with the present invention will provide a safe method of jacking drilling platforms providing a gripping force upon the platform leg which is proportional to the weight of the drilling platform.

Leveling of a drilling platform is simple and safe. A jacking distance of a fraction of an inch may be achieved, if desired, because one sheet of jaws can grip the platform leg at any point along the leg, while actuation means can be used to slide the platform any desired distance along the platform leg. Gripping is automatic. The jacking distance is not constrained by any requirement that shear pin holes be aligned or that gears be meshed. The platform may be jacked up or leveled without completely releasing any one of the platform legs.

Thus, it is apparent that there has been provide in accordance with the invention, a cylinder gripping apparatus that substantially incorporates the advantages set forth above. Although the present invention has been described in conjunction with specific forms thereof, it is evident that many alternatives, modifications, and variations will be apparent to those skilled in the art in light of the foregoing disclosure. Accordingly, this description is to be construed as illustrative only and is for the purpose of teaching those skilled in the art the manner of carrying out the invention. It is to be understood that the forms of the invention herewith shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

It will be appreciated that in constructing a hydrostatic testing apparatus according to the present invention, certain significant advantages are provided.

In particular, a hydrostatic testing apparatus according to the present invention permits the hydrostatic testing of a vareity of pipe sizes with a single testing apparatus. In addition, pipe with a bell end, coupling end or upset portion may be effectively capped by the apparatus. An apparatus according to the present invention permits the axial centering of various sizes of pipe, and permits axial centering of pipe having an upset portion, bell end or coupling end.

A hydrostatic testing apparatus according to the present invention permits the expungement of air or other gas from the interior pressurized zone of the pipe and apparatus, thus reducing the hazard of explosion during testing.

A hydrostatic testing apparatus with replaceable jaw tooth segments is provided to facilitate effective gripping of various pipe sizes and to facilitate the replacement of worn jaws. A jaw tooth assembly is provided utilizing parallel arms and a pin mounting which is parallel to the axis of the pipe, and dual parallel links are provided for coupling to the body. This construction permits a more economical and practical hydrostatic testing apparatus to be constructed utilizing only two jaws to grip the pipe. The parallel mounted pin facilitates the more even distribution of a gripping force to the pipe, thus minimizing hoop stresses upon the pipe.

A hydrostatic testing apparatus constructed with a tension member in the rear zone of the apparatus provides the advantage of an apparatus which may be constructed more economically and with less reinforcement in the sides of the apparatus.

The invention provides a fluid-tight seal even for pipe that is dirty, rusty, or rough. A seal according to the present invention provides the additional advantage of being pre-stressed to provide a fluidtight seal with the pipe even under low pressure. A seal according to the present invention has the advantage of permitting itself to be flushed during successive hydrostatic tests, thereby removing dirt and other foreign matter from between the lips of the seal.

A hydrostatic testing apparatus according to the present invention includes the further advantage of providing a seal adapted for high pressure testing. A sealing ring inhibits the extrusion of the flexible seal during high pressure testing.

A hydrostatic testing apparatus according to the present invention provides a holding force for holding the apparatus onto the end of the pipe where the holding force is generated by the internal pressure of the fluid in the pipe, and which is larger and proportional to the internal pressure. A mechanism is provided for evenly distributing the holding force across the outer surface of the pipe.

Thus it is apparent that there has been provided in accordance with the invention, a hydrostatic testing apparatus that substantially incorporates the advantages set forth above. Although the present invention has been described in conjunction with specific forms thereof, it is evident that many alternatives, modifications, and variations will be apparent to those skilled in the art in light of the foregoing disclosure. Accordingly, this description is to be construed as illustrative only and is for the purpose of teaching those skilled in the art the manner of carrying out the invention. It is to be understood that the forms of the invention herewith shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

What is claimed is:

1. A cylinder gripping apparatus, comprising:
   a jaw, said jaw having a friction surface adapted for gripping a cylinder;
   a body, said body being adapted to axially receive the cylinder, said body having a front and a rear;
   an interfacing assembly, said interfacing assembly being interposed between said jaw and said body, said interfacing assembly being adapted to urge said jaw into gripping engagement with the cylinder when said jaw is urged generally rearwardly with respect to said body, said interfacing assembly being adapted to provide a radial counterforce in response to an axial force upon the cylinder, said radial counterforce being proportional to said axial force, said interfacing assembly having a curved surface on one end of said interfacing assembly, said curved surface being cooperable with an opposing face to permit a transverse displacement of said jaw from an initial position to a displaced position.

2. The apparatus according to claim 1, wherein said opposing face comprises a planar surface upon said jaw, said planar surface being located upon a side of said jaw generally opposite to said friction surface of said jaw.

3. The apparatus according to claim 1, wherein said opposing face comprises a curved surface upon said jaw, said curved surface being located upon a side of said jaw generally opposite to said friction surface of said jaw.

4. The apparatus according to claim 1, wherein said opposing face comprises a curved surface being adapted to receive said end of said interfacing assembly having said curved surface.

5. The apparatus according to claim 1, wherein said opposing face comprises a planar surface upon said body.

6. A cylinder gripping apparatus, comprising:
   a jaw, said jaw having a friction surface adapted for gripping a cylinder, said jaw having a first bearing groove;
   a body, said body being adapted to axially receive the cylinder, said body having a side wall, said side wall of said body having a second bearing groove, said body having a front and a rear; and,
   an angularly disposed floating force translation lug, said lug being engageable in said first and second bearing grooves, said lug being adapted to operatively associate said jaw with said body, said lug being adapted to urge said jaw into gripping engagement with the cylinder when said jaw is urged generally rearwardly with respect to said body, said lug being adapted to permit said jaw to disengage the cylinder when said jaw is urged generally forwardly with respect to said body.

7. The apparatus to claim 6, further comprising:
   a first stay connected to said jaw, said first stay being adapted to cover at least a portion of a cross sectional area of said first bearing groove in said jaw, said first stay being adapted to laterally retain said lugs within said first bearing groove while leaving said lugs free to rotatively pivot within said first bearing groove; and
   a second stay connected to said side wall of said body, said second stay being adapted to cover at least a portion of a cross sectional area of said second bearing surface in said side wall, said second stay being adapted to laterally retain said lugs within said second bearing groove while leaving said lugs free to rotatively pivot within said second bearing groove.

8. The apparatus according to claim 7, further comprising:
   a resilient member disposed against said body, said resilient member being interposed between said body and said jaw, said resilient member being adapted to urge said jaw into engagement with the cylinder.

9. The apparatus according to claim 8, further comprising:
   actuating means connected to said lug for rotationally pivoting said lug whereby said jaw is urged generally forwardly permitting said jaw to disengage the cylinder; and,
   an elastic member connected between said side wall of said body and said jaw, said elastic member being adapted to urge said jaw radially outward, said elastic member being adapted to urge said lug into operative engagement with said first and second bearing grooves.

10. The apparatus according to claim 9, wherein:
    said first bearing groove comprises a first arcuate bearing surface and further comprises a sloped forward surface, said forward surface being adapted to permit said lug to rotate in a first sense with respect to said jaw;
    said second bearing groove comprises a second arcuate bearing surface and further comprises a sloped rearward surface, said rearward surface being adapted to permit said lug to rotate in a first sense with respect to said sidewall of said body;
    said lug having a first arcuate end and a second arcuate end, said first arcuate end being adapted to substantially contiguously engage said first arcuate bearing surface of said first bearing groove, said second arcuate end being adapted to substantially contiguously engage said second arcuate bearing surface of said second bearing groove, said lug being rotatably engageable against said first and second arcuate bearing surfaces.

11. A hydrostatic testing apparatus for capping an open end of a pipe comprising:
 a jaw, said jaw having a first bearing groove, said jaw having a friction surface adapted for gripping the pipe;
 a body, said body being adapted to axially receive a pipe, said body having a second bearing groove; and,
 a force translation lug, said lug being unconnected to said body and said jaw, said lug being disposable against said body and against said jaw, said lug being adapted to rotatively engage within said first and second bearing grooves, said lug being operable to urge said friction surface of said jaw against an outside surface of the pipe when said lug is rotated in a first sense with respect to said body.

12. The apparatus according to claim 11, said body having an interior zone, further comprising:
 a purge valve connected to said body; and,
 a passageway to place said purge valve in fluid communication with the interior zone of said body.

13. The apparatus according to claim 11, further comprising:
 a seal axially positioned within said body and adapted to form a hydraulic seal between said body and the pipe to be capped, said seal having a first lip disposable against the inner surface of said body, the seal having a second lip connected to said first lip and adapted to displace toward an outer surface of the pipe to be capped.

14. A cylinder gripping apparatus, comprising:
 a body, said body being adapted to axially receive a cylinder, said body having a side wall, said side wall having an inclined inner surface;
 a jaw, said jaw having a friction surface adapted to grip the cylinder;
 a plurality of generally cylindrical rollers, said rollers being unconnected to said jaw and said body, said rollers being interposed between said jaw and said body, said rollers being operable to facilitate the movement of said jaw relative to said body along said inclined inner surface, said inclined inner surface being adapted to urge said jaw into engagement with an outer surface of the cylinder when said jaw is urged rearwardly with respect to said body.

15. The apparatus according to claim 14, further comprising:
 a plurality of channels formed traversely along said inclined inner surface, said channels being adapted to receive said rollers, said channels being generally cylindrically shaped in substantial correspondence with the shape of said rollers.

16. The apparatus according to claim 14, further comprising:
 a plurality of channels formed transversely along said jaw upon a surface of said jaw generally opposite said friction surface, said channels being adapted to receive said rollers, said channels being generally cylindrically shaped in substantial correspondence with the shape of said rollers.

17. The apparatus according to claim 15 or 16, further comprising:
 a resilient member disposed against said body, said resilient member being adapted to urge said jaw into engagement with the cylinder;
 actuating means pivotally connected to said body for urging said jaw generally forwardly with respect to said body; and,
 an elastic member connected between said body and said jaw, said elastic member being adapted to urge said jaw radially outwardly toward said body into operative engagement with said rollers, said elastic member being operable to maintain said rollers within said channels.

18. A cylinder gripping apparatus, comprising:
 a body, said body being adapted to axially receive a cylinder;
 a cam arm pivotally attached to said body, said cam arm having a generally arcuate cam surface; and,
 a jaw, said jaw having a friction surface adapted for gripping the cylinder, said jaw having a groove in a surface generally opposite to said friction surface, said groove being adapted to receive said cam arm, said cam arm being operable to urge said jaw into engagement with an outer surface of the cylinder when said cam arm is rotated with respect to said body.

19. The apparatus according to claim 18, further comprising:
 a plurality of elastic members, connected between said body and said jaw, said elastic members being adapted to urge said jaw radially outward toward said body, said elastic members being operable to urge said jaw into operative engagement with said cam arm;
 a forward alignment lip connected to the forward edge of said jaw; and,
 a rear alignment lip connected to the rear edge of said jaw.

20. A cylinder gripping apparatus, comprising:
 a jaw, said jaw having a friction surface adapted for gripping a cylinder, said jaw being adapted to dispose against a force translation lug;
 a body, said body being adapted to axially receive the cylinder, said body having a side wall, said side wall of said body being adapted to dispose against a force translation lug, said body having a front and a rear; and,
 an angularly disposed force translation lug, said lug having at least one generally spherical end, said lug being interposed between said body and said jaw, said lug being adapted to urge said jaw into gripping engagement with the cylinder when said jaw is urged generally rearwardly with respect to said body, said spherical end of said lug being adapted to engage a generally corresponding spherical groove, said spherical end and said spherical groove being operable to permit said jaw to engage the cylinder in generally corresponding alignment with the cylinder.

21. The apparatus according to claim 20, wherein:
 said spherical groove is located upon said side wall of said body; and
 said force translation lug is pivotally connected to said jaw.

22. The apparatus according to claim 20, wherein:
 said spherical groove is located upon said jaw; and
 wherein said force translation lug is pivotally connected to said side wall of said body.

23. The apparatus according to claim 20, wherein:

said force translation lug further comprises a second generally spherical end remote from said first spherical end; and, said spherical groove is located upon said side wall of said body;

and further comprising:

a second spherical groove generally corresponding to said second spherical end, said second spherical groove being located upon said jaw, said ends of said force translation lug being adapted to engage said grooves, said force translation lug being operable to permit radial, axial and transverse movement of said jaw with respect to said body.

24. A platform jacking apparatus, comprising:

a body, said body being connectable to a platform, said body having a guide sleeve, said body being adapted to axially receive a platform leg, a first set of jaws, said jaws being adapted to grip the platform leg, said jaws being in operative association with said body, said jaws being adapted to provide a first radial counterforce in response to an axial force upon the platform leg, said first radial counterforce being proportional to said axial force, a jaw housing, said jaw housing being adapted to axially receive the platform leg, said jaw housing being adapted to coaxially fit within said guide sleeve of said body, said jaw housing being adapted to reciprocally slide within said guide sleeve, a second set of jaws, said jaws being adapted to grip the platform leg, said jaws being in operative association with said jaw housing, said jaws being adapted to provide a second radial counterforce in response to said axial force, said second radial counterforce being proportional to said axial force, actuation means connected to said body and disposed against said jaw housing for reciprocally moving said jaw housing within said guide sleeve, said actuation means being operable to extend and retract said jaw housing within said guide sleeve;

said first jaws being mutually cooperable with said second jaws and said actuation means to grip the platform leg when said second jaws are disengaged from the platform leg and said jaw housing is being retracted by said actuation means; and, said second jaws and said actuation means being mutually cooperable with said first jaws to grip the platform leg when said first jaws are disengaged from the platform leg and said jaw housing is being extended by said actuation means, said actuation means, said second jaws, said jaw housing, and said body being operable to raise the platform when said jaw housing is extended by said actuation means.

25. The apparatus according to claim 24, further comprising:

a first releaser, said first releaser being connected to said body, said first releaser being in operative association with said first jaws, said first releaser being operable to disengage said first jaws from the platform leg to permit said actuation means to extend said jaw housing and raise the platform;

a second releaser, said second releaser being connected to said jaw housing, said second releaser being in operative association with said second jaws, said second releaser being operable to disengage said second jaws from the platform leg to permit said actuation means to retract said jaw housing.

26. A member gripping apparatus for gripping a member having a predetermined cross-sectional shape, comprising:

a jaw, said jaw having a friction surface adapted for gripping a member, said friction surface generally conforming to the shape of the member to be gripped;

a body, said body being adapted to axially receive the member, said body having a front and a rear;

an interfacing assembly, said interfacing assembly being interposed between said jaw and said body, said interfacing assembly being adapted to urge said jaw into gripping engagement with the member when said jaw is urged generally rearwardly with respect to said body, said interfacing assembly being adapted to provide a radial counterforce in response to an axial force upon the member, said radial counterforce being proportional to said axial force, said interfacing assembly having a curved surface on one end of said interfacing assembly, said curved surface being cooperable with an opposing face to permit a transverse displacement of said jaw from an initial position to a displaced position.

27. The apparatus according to claim 26, wherein said opposing face comprises a planar surface upon said jaw, said planar surface being located upon a side of said jaw generally opposing to said friction surface of said jaw.

28. The apparatus according to claim 26, wherein said opposing face comprises a curved surface upon said jaw, said curved surface being located upon a side of said jaw generally opposite to said friction surface of said jaw.

29. The apparatus according to claim 26, wherein said opposing face comprises a curved surface being adapted to receive said end of said interfacing assembly having said curved surface.

30. The apparatus according to claim 26, wherein said opposing face comprises a planar surface upon said body.

31. A member gripping apparatus, comprising:

a jaw, said jaw having a friction surface adapted for gripping a member, said jaw having a first bearing groove;

a body, said body being adapted to axially receive the member, said body having a side wall, said side wall of said body having a second bearing groove, said body having a front and a rear; and, an angularly disposed floating force translation lug, said lug being engagable in said first and second bearing grooves, said lug being adapted to operatively associate said jaw with said body, said lug being adapted to urge said jaw into gripping engagement with the member when said jaw is urged generally rearwardly with respect to said body, said lug being adapted to permit said jaw to disengage the member when said jaw is urged generally forwardly with respect to said body.

32. The apparatus according to claim 31, further comprising:

a first stay connected to said jaw, said first stay being adapted to cover at least a portion of a cross sectional area of said first bearing groove in said jaw, said first stay being adapted to laterally retain said lugs within said first bearing groove while leaving said lugs free to rotively pivot within said first bearing groove; and, a second stay connected to said side wall of said body, said second stay being adapted to cover at least a portion of a cross sectional area of said second bearing surface in said side wall, said second stay being adapted to laterally retain said lugs within said second bearing groove while leaving said lugs free to rotatively pivot within said second bearing groove.

33. The apparatus according to claim 32, further comprising:
a resilient member disposed against said body, said resilient member being interposed between said body and said jaw, and resilient member being adapted to urge said jaw into engagement with the member.

34. The apparatus according to claim 33, further comprising:
actuating means connected to said lug for rotationally pivoting said lug whereby said jaw is urged generally forwardly permitting said jaw to disengage the member; and,
an elastic member connected between said side wall of said body and said jaw, said elastic member being adapted to urge said jaw radially outwardly, said elastic member being adapted to urge said lug into operative engagement with said first and second bearing grooves.

35. The apparatus according to claim 34, wherein:
said first bearing groove comprises a first actuate bearing surface and further comprises a sloped forward surface, said forward surface being adapted to permit said lug to rotate in a first sense with respect to said jaw;
said second bearing groove comprises a second arcuate bearing surface and further comprises a sloped rearward surface, said rearward surface being adapted to permit said lug to rotate in a first sense with respect to said sidewall of said body; and,
said lug having a first arcuate end and a second arcuate end, said first arcuate end being adapted to substantially engage said first arcuate bearing surface of said first bearing groove, said second arcuate end being adapted to substantially contiguously engage said second arcuate bearing surface of said second bearing groove, said lug being rotatably engagable against said first and second arcuate bearing surfaces.

36. A member gripping apparatus for gripping a member having a predetermined cross-sectional shape, comprising:
a body, said body being adapted to axially receive a member, said body having a side wall, said side wall having an inclined inner surface;
a jaw, said jaw having a friction surface adapted to grip the member, said friction surface generally conforming to the shape of an outer surface of the member to be gripped;
a plurality of generally cylindrical rollers, said rollers being unconnected to said jaw and said body, said rollers being interposed between said jaw and said body, said rollers being operable to facilitate the movement of said jaw relative to said body along said inclined inner surface, said inclined inner surface being adapted to urge said jaw into engagement with the outer surface of the member when said jaw is urged rearwardly with respect to said body.

37. The apparatus according to claim 36, further comprising:
a plurality of channels formed traversely along said inclined inner surface, said channels being adapted to receive said rollers, said channels being generally cylindrically shaped in substantial correspondence with the shape of said rollers.

38. The apparatus according to claim 36, further comprising:
a plurality of channels formed transversely along said jaw upon a surface of said jaw generally opposite said friction surface, said channels being adapted to receive said rollers, said channels being generally cylindrically shaped in substantial correspondence with the shape of said rollers.

39. The apparatus according to claim 37 or claim 38, further comprising:
a resilient member disposed against said body, said resilient member being adapted to urge said jaw into engagement with the member to be gripped;
actuating means pivotally connected to said body for urging said jaw generally forwardly with respect to said body; and,
an elastic member connected between said body and said jaw, said elastic member being adapted to urge said jaw radially outwardly toward said body into operative engagement with said rollers, said elastic member being operable to maintain said rollers within said channels.

40. A bar gripping apparatus for gripping a bar having a predetermined cross-sectional shape, comprising:
a body, said body being adapted to axially receive a bar;
a cam arm pivotally attached to said body, said cam arm having a generally arcuate cam surface; and,
a jaw, said jaw having a friction surface adapted for gripping the bar, said friction surface being adapted to conform to the shape of an outer surface of the bar, said jaw having a groove in a surface generally opposite to said friction surface, said groove being adapted to receive said cam arm, said cam arm being operable to urge said jaw into engagement with the outer surface of the bar when said cam arm is rotated with respect to said body.

41. The apparatus according to claim 40, further comprising:
a plurality of elastic members, connected between said body and said jaw, said elastic members being adapted to urge said jaw radially outward toward said body, said elastic members being operable to urge said jaw into operative engagement with said cam arm;
a forward alignment lip connected to the forward edge of said jaw; and,
a rear alignment lip connected to the rear edge of said jaw.

42. A member gripping apparatus, comprising:
a jaw, said jaw having a friction surface adapted for gripping a member, said jaw being adapted to dispose against a force translation lug;
a body, said body being adapted to axially receive the member, said body having a side wall, said side wall of said body being adapted to dispose against a force translation lug, said body having a front and a rear; and,
an angularly disposed force translation lug, said lug having at least one generally spherical end, said lug being interposed between said body and said jaw, said lug being adapted to urge said jaw into gripping engagement with the member when said jaw is urged generally rearwardly with respect to said body, said spherical end of said lug being adapted to engage a generally corresponding spherical groove, said spherical end and said spherical groove being operable to permit said jaw to engage the member in generally corresponding alignment with the member.

43. The apparatus according to claim 42, wherein:
said spherical groove is located upon said side wall of said body; and,
said force translation lug is pivotally connected to said jaw.

44. The apparatus according to claim 42, wherein:
said spherical groove is located upon said jaw; and,
wherein said force translation lug is pivotally connected to said side wall of said body.

45. The apparatus according to claim 42, wherein:
said force translation lug further comprises a second generally spherical end remote from said first spherical end; and,
said spherical groove is located upon said side wall of said body;
and further comprising:
a second spherical groove generally corresponding to said second spherical end, said second spherical groove being located upon said jaw, said ends of said force translation lug being adapted to engage said grooves, said force translation lug being operable to permit radial, axial and transverse movement of said jaw with respect to said body.

* * * * *